(12) United States Patent
Holdmeyer et al.

(10) Patent No.: US 12,419,702 B2
(45) Date of Patent: Sep. 23, 2025

(54) MECHANICALLY DECOUPLED CLOSURE SUBSYSTEM

(71) Applicant: Cilag GmbH International, Zug (CH)

(72) Inventors: Seth Daniel Holdmeyer, Sharonville, OH (US); Jeffrey L. Clark, Maineville, OH (US); Eric William Brunner, Cincinnati, OH (US); Maria Lupp, Cincinnati, OH (US); Jalen Lee Wize, Cincinnati, OH (US); Grant Wood Nair, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 539 days.

(21) Appl. No.: 17/852,261

(22) Filed: Jun. 28, 2022

(65) Prior Publication Data

US 2023/0414300 A1 Dec. 28, 2023

(51) Int. Cl.
*A61B 34/30* (2016.01)
*A61B 34/00* (2016.01)
*B25J 9/10* (2006.01)
*B25J 17/02* (2006.01)

(52) U.S. Cl.
CPC ............ *A61B 34/30* (2016.02); *B25J 9/106* (2013.01); *B25J 17/02* (2013.01); *A61B 2034/301* (2016.02); *A61B 2034/302* (2016.02); *A61B 2034/303* (2016.02); *A61B 2034/306* (2016.02); *A61B 2034/715* (2016.02)

(58) Field of Classification Search
None
See application file for complete search history.

(56) References Cited

U.S. PATENT DOCUMENTS

| | | | |
|---|---|---|---|
| 9,259,275 B2* | 2/2016 | Burbank | A61B 34/76 |
| 2015/0342585 A1* | 12/2015 | Steege | A61B 17/3201 606/1 |
| 2018/0206904 A1* | 7/2018 | Felder | A61B 46/10 |
| 2020/0138507 A1* | 5/2020 | Davison | A61B 17/29 |
| 2021/0022819 A1* | 1/2021 | Duque | A61B 34/71 |
| 2023/0053012 A1* | 2/2023 | Fagan | A61B 17/320092 |
| 2025/0009413 A1* | 1/2025 | Whitlock | A61B 17/07207 |

* cited by examiner

*Primary Examiner* — Jennifer Pitrak McDonald
*Assistant Examiner* — Michael T. Holtzclaw
(74) *Attorney, Agent, or Firm* — Vorys, Sater, Seymour and Pease LLP

(57) ABSTRACT

A surgical tool includes an elongate shaft, an end effector arranged at a distal end of the shaft and including opposing jaws, and an articulable wrist interposing the end effector and the shaft and comprising a plurality of articulation links arranged in series along a longitudinal length of the wrist. A closure redirect mechanism includes first and second rigid links arranged proximal to the wrist, first and second transfer mechanisms pivotably mounted to the first and second rigid links, respectively, first and second transfer links interposing the end effector and the wrist, and first and second tension members extending distally from the first and second transfer mechanisms, respectively, and being secured to the first and second transfer links, respectively. Moving the first rigid link relative to the second rigid link, and vice versa, causes the first and second transfer links to correspondingly move and thereby open or close the jaws.

21 Claims, 26 Drawing Sheets

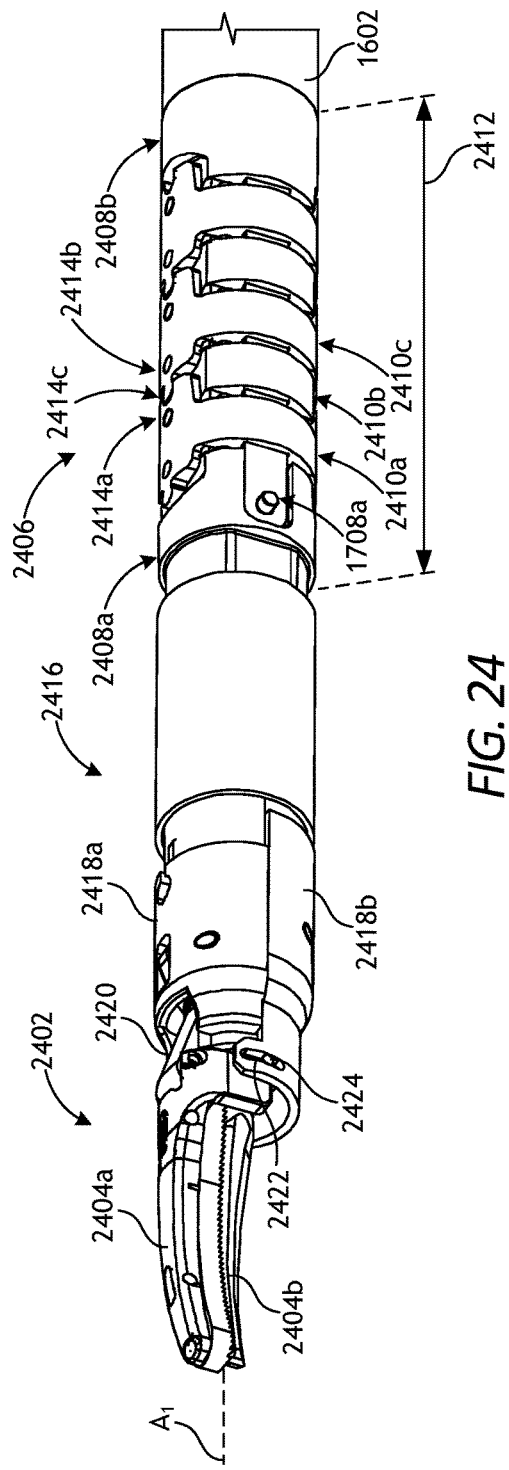
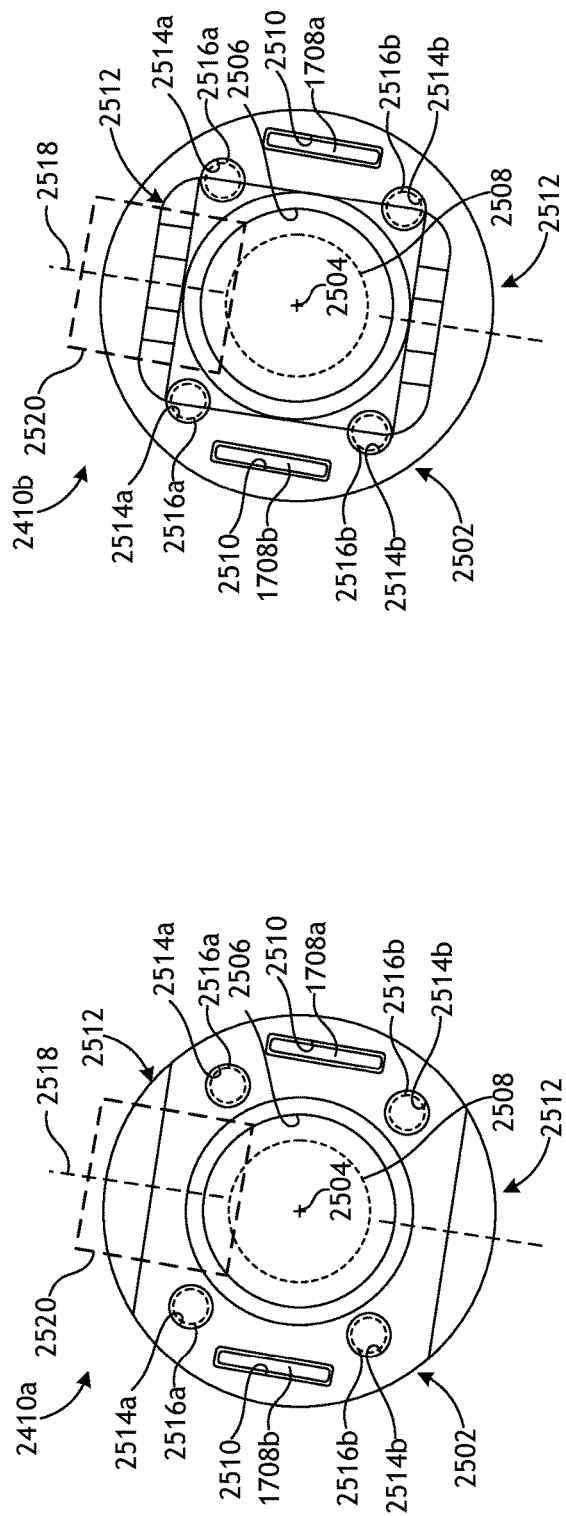
FIG. 24
FIG. 25B
FIG. 25A

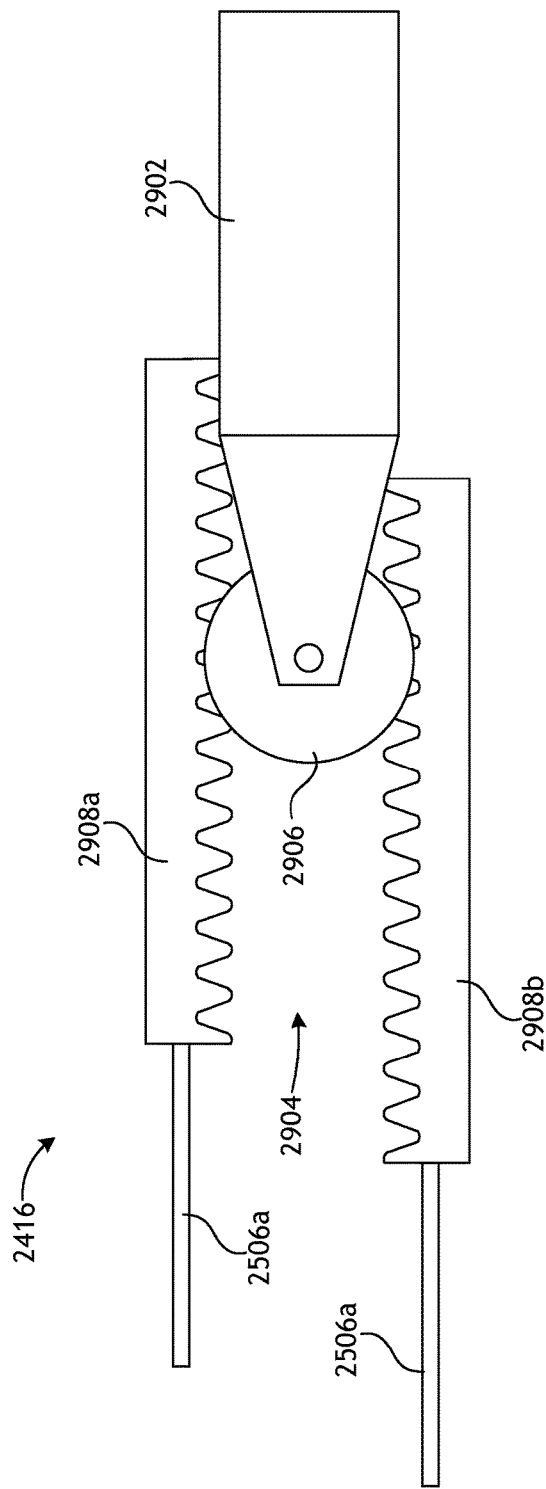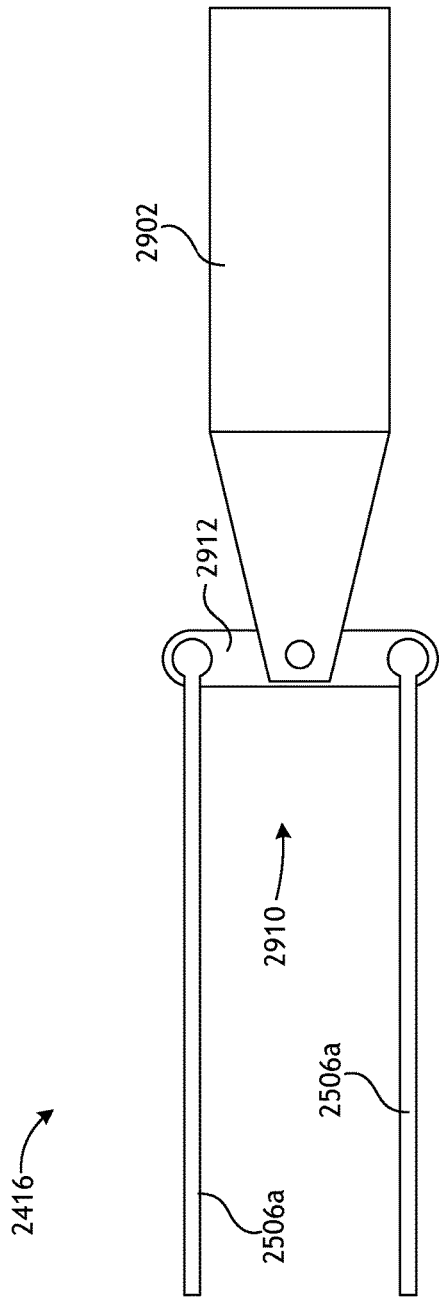
FIG. 29A
FIG. 29B

MECHANICALLY DECOUPLED CLOSURE SUBSYSTEM

TECHNICAL FIELD

The systems and methods disclosed herein are directed to robotic surgical tools and, more particularly to, articulable wrists for surgical tools that include multiple articulation links pivotably coupled and arranged in series.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar are used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables (or other elongate members) that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system and thereby actively controlling the tension balance in the drive cables. Moving the drive cables articulates the end effector to desired angular positions and configurations.

Improvements to robotically-enabled medical systems will provide physicians with the ability to perform endoscopic and laparoscopic procedures more effectively and with improved ease.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 24 is an enlarged isometric view of the distal end of the surgical tool of FIG. 16, according to one or more additional embodiments.

FIG. 25A is a cross-sectional end view of the first articulation link of FIG. 24, according to one or more embodiments.

FIG. 25B is a cross-sectional end view of the third articulation link of FIG. 24, according to one or more embodiments.

FIGS. 29A and 29B are enlarged, schematic views of alternate embodiments of the proximal end of the closure redirect mechanism of FIG. 24, according to one or more embodiments.

DETAILED DESCRIPTION

1. Overview.

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance, to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto, as such concepts may have applicability throughout the entire specification.

A. Robotic System—Cart.

Figure 1:
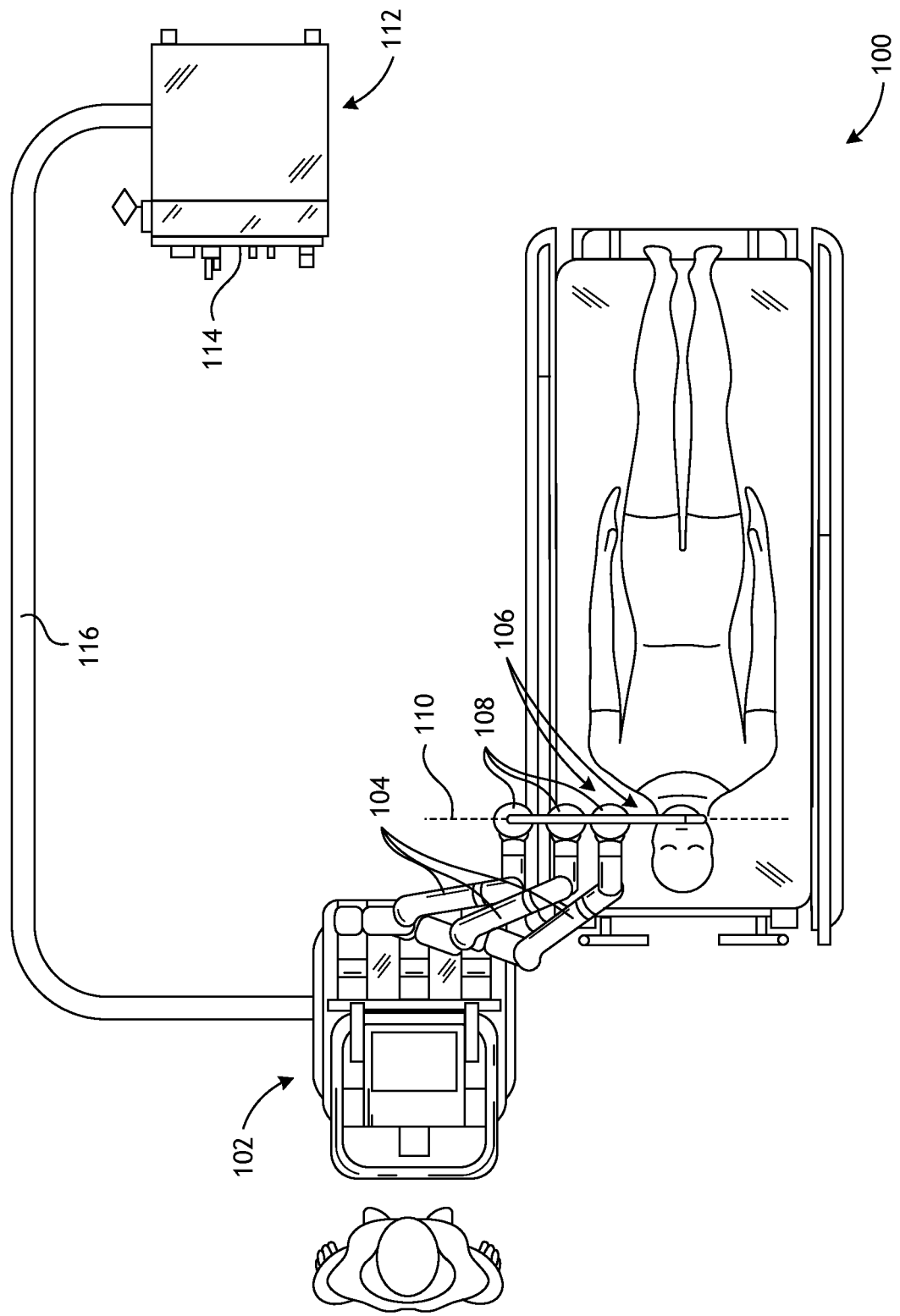
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastrointestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or re-positioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
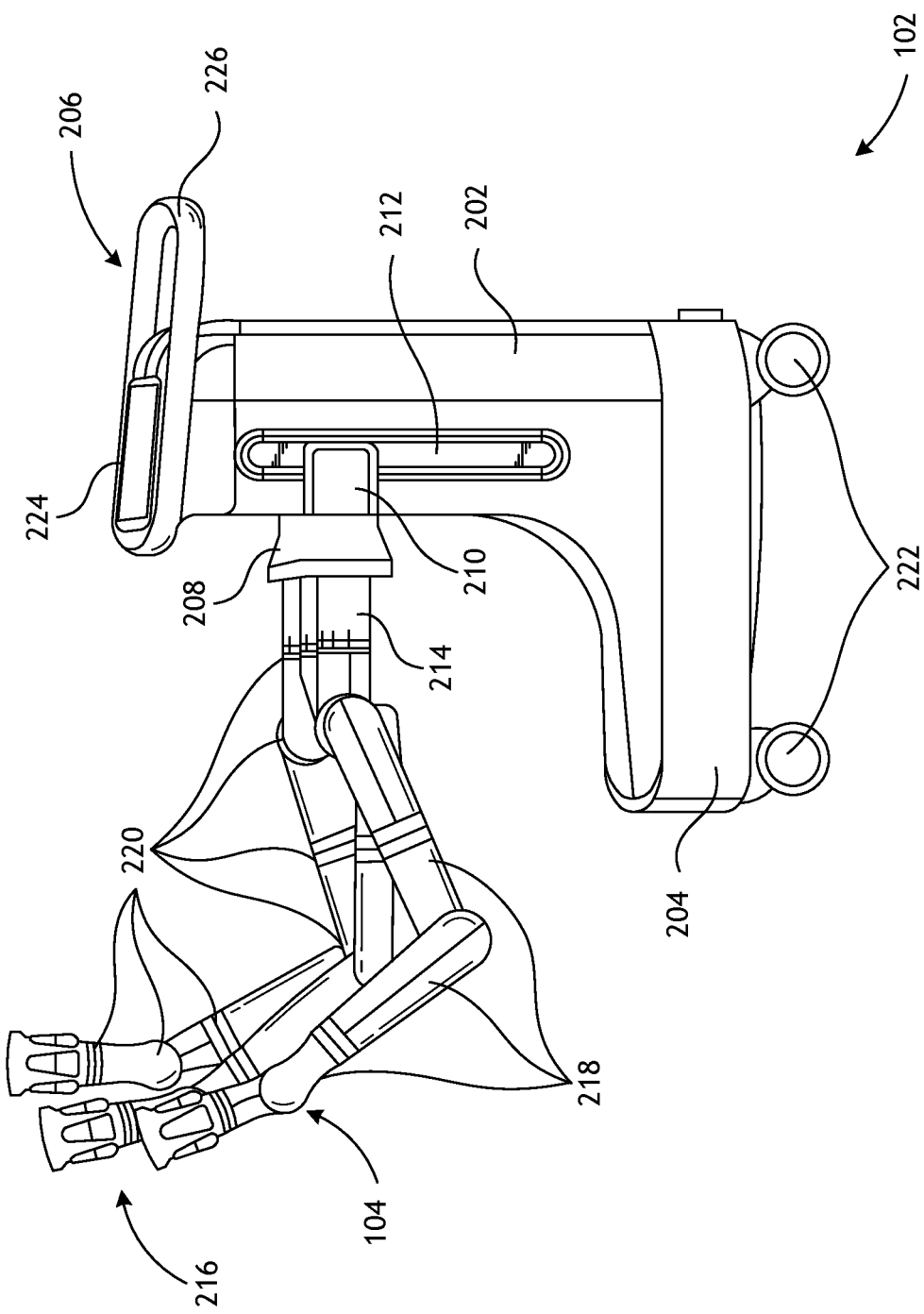
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, which are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, the carriage 208, and the arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
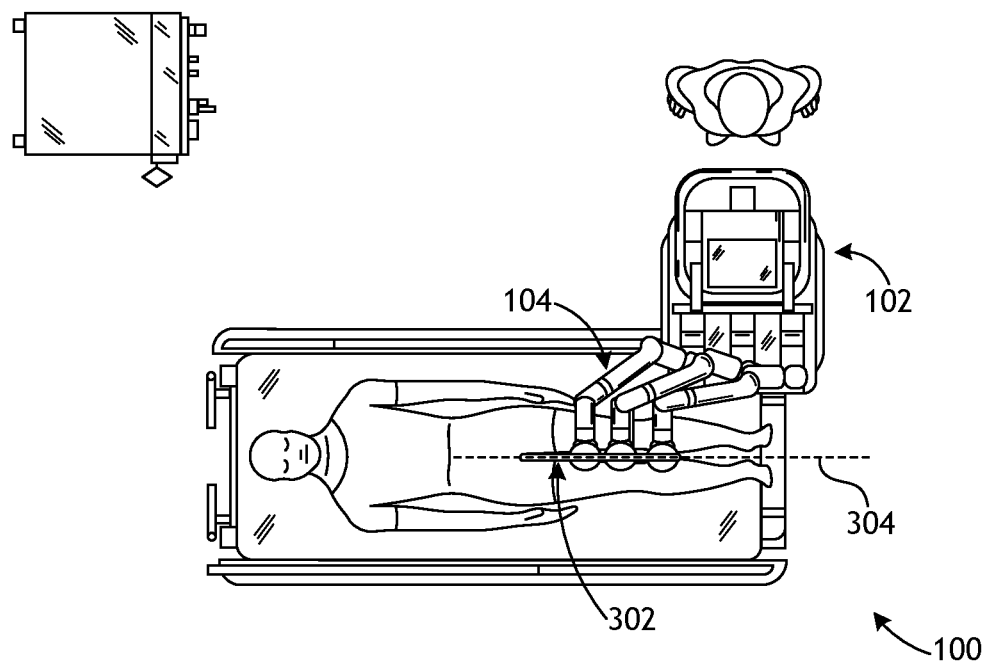
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
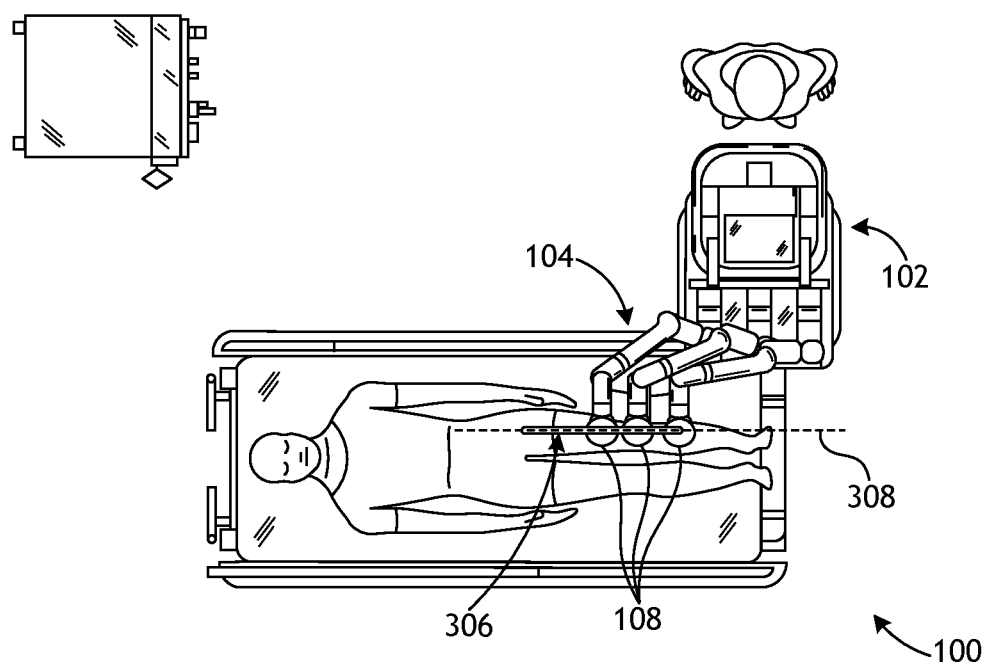
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
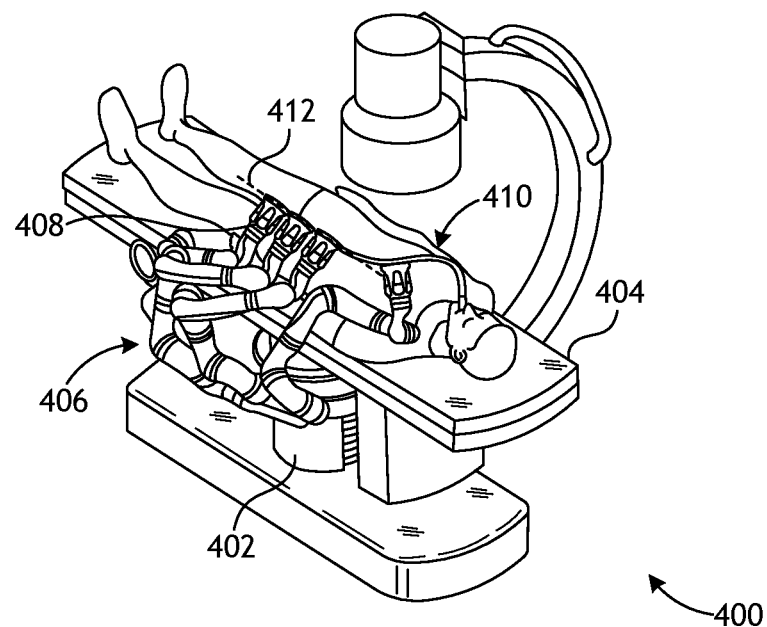
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
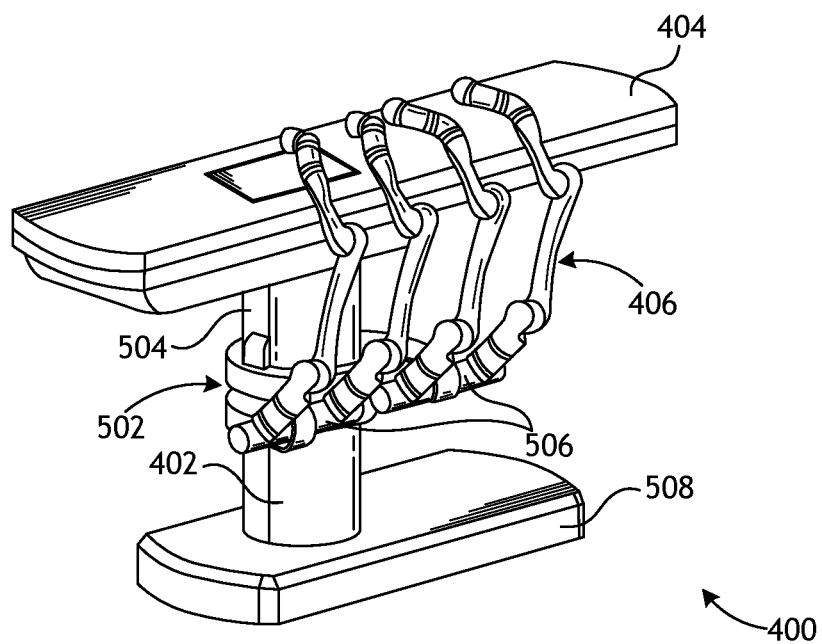
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
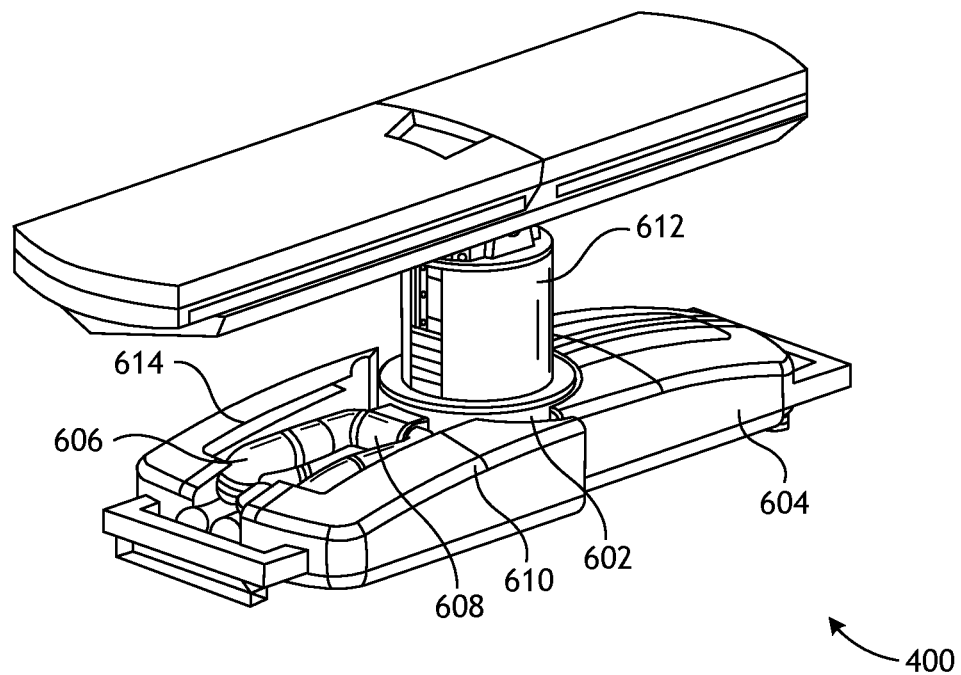
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
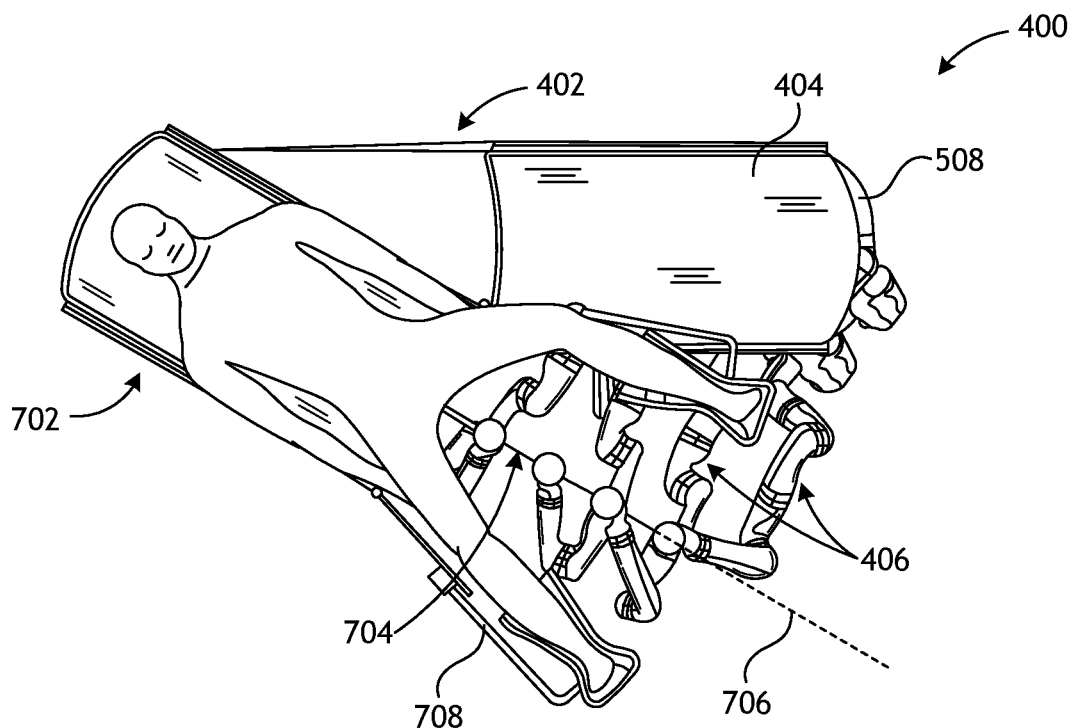
FIG. 7A illustrates an embodiment of a table-based robotic system configured for a ureteroscopy procedure.
Figure 7B:
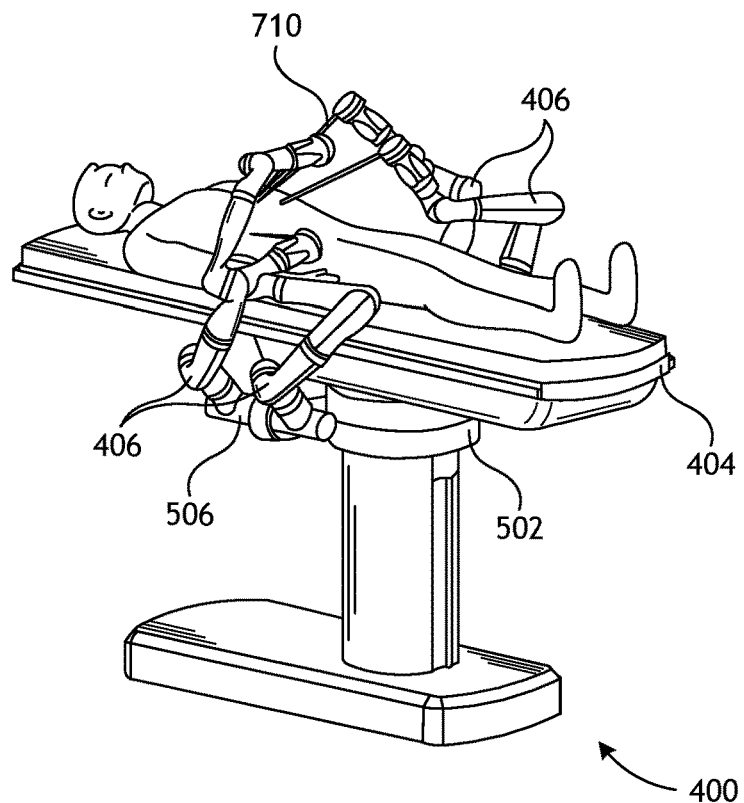
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
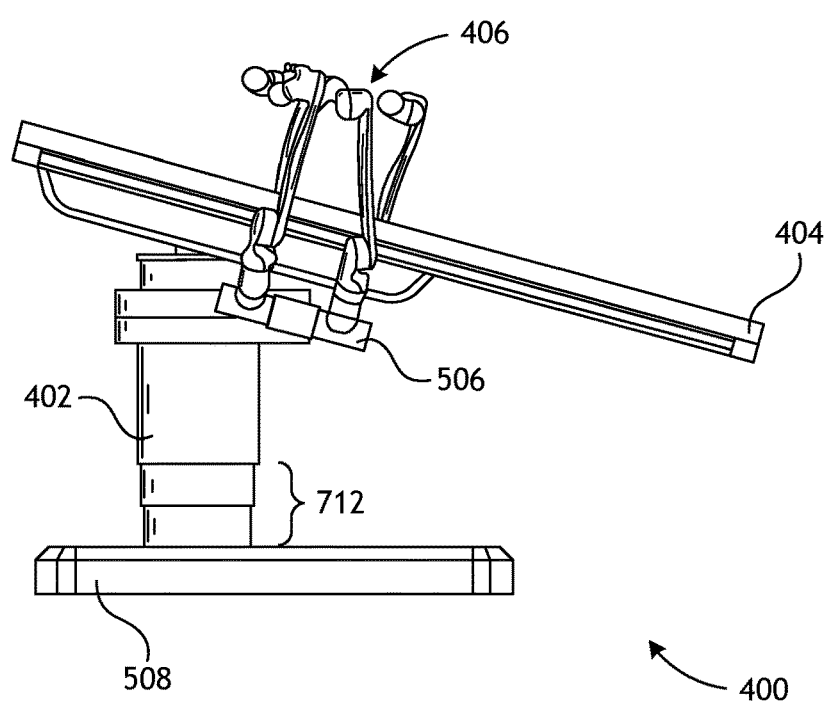
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
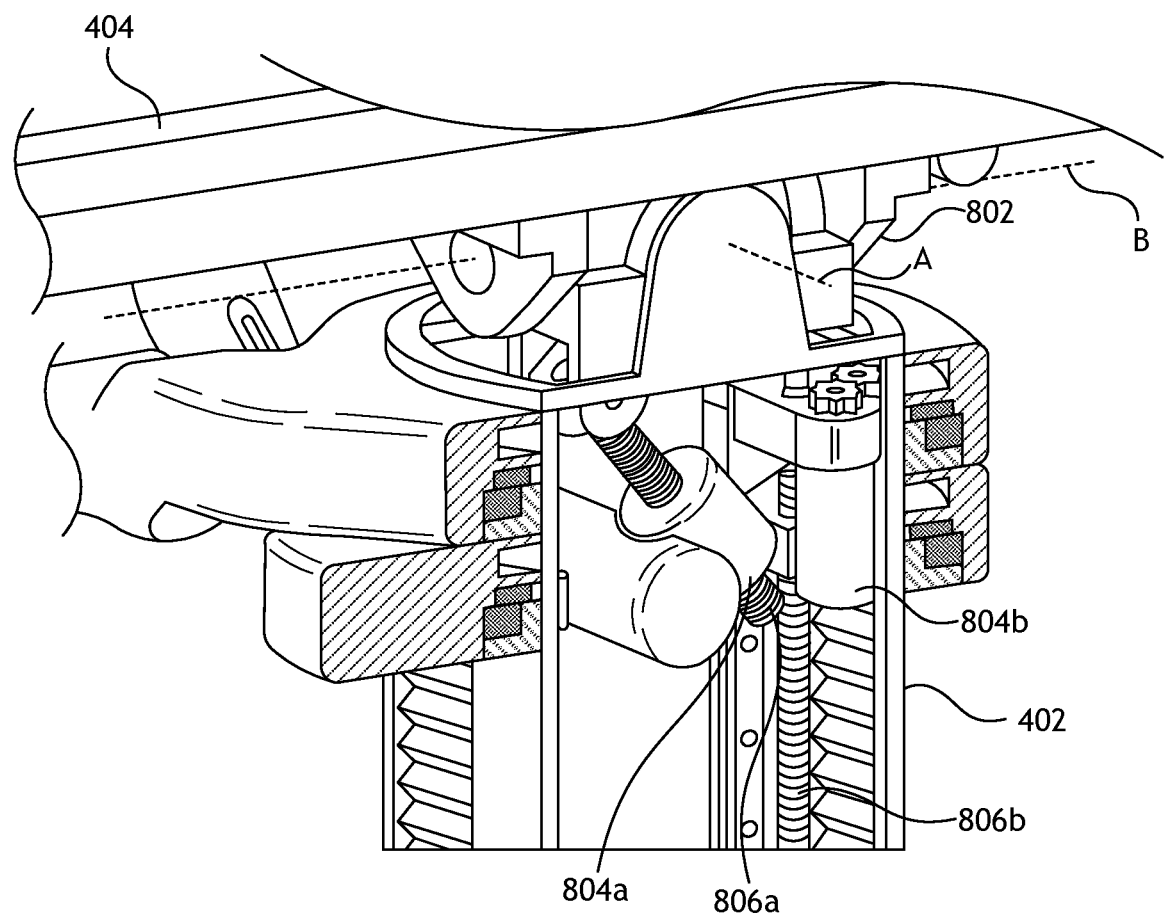
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
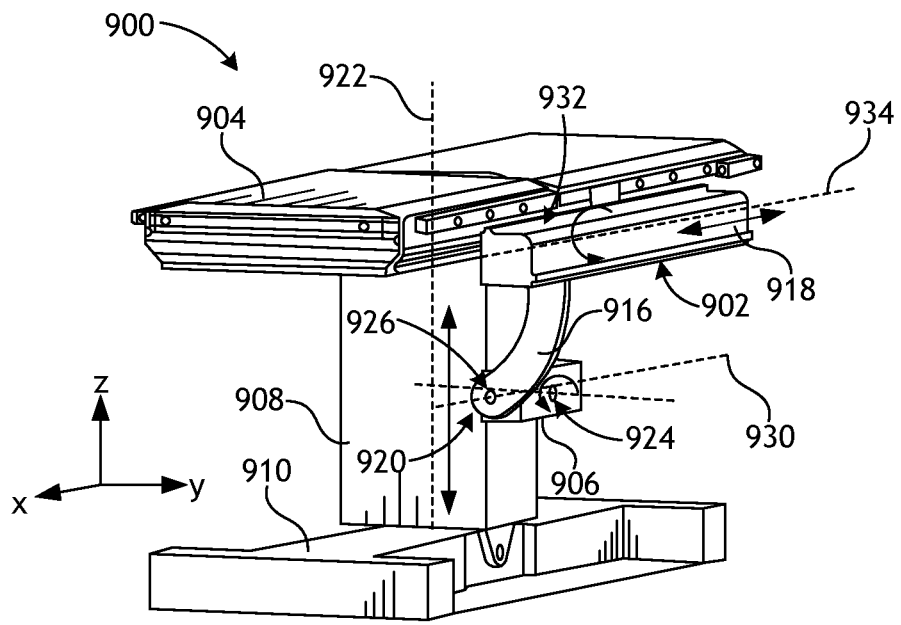
FIG. 9A illustrates an alternative embodiment of a table-based robotic system.
Figure 9B:
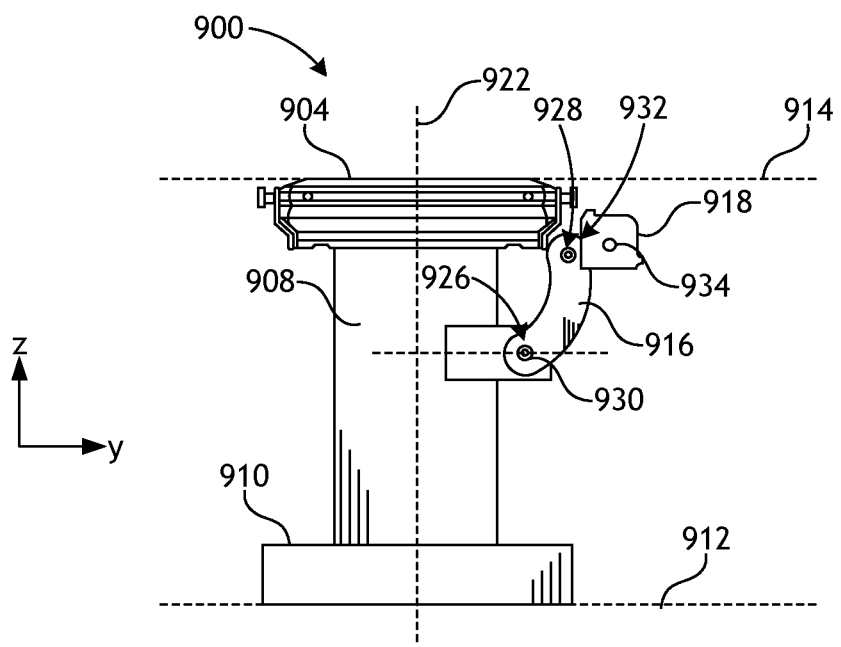
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
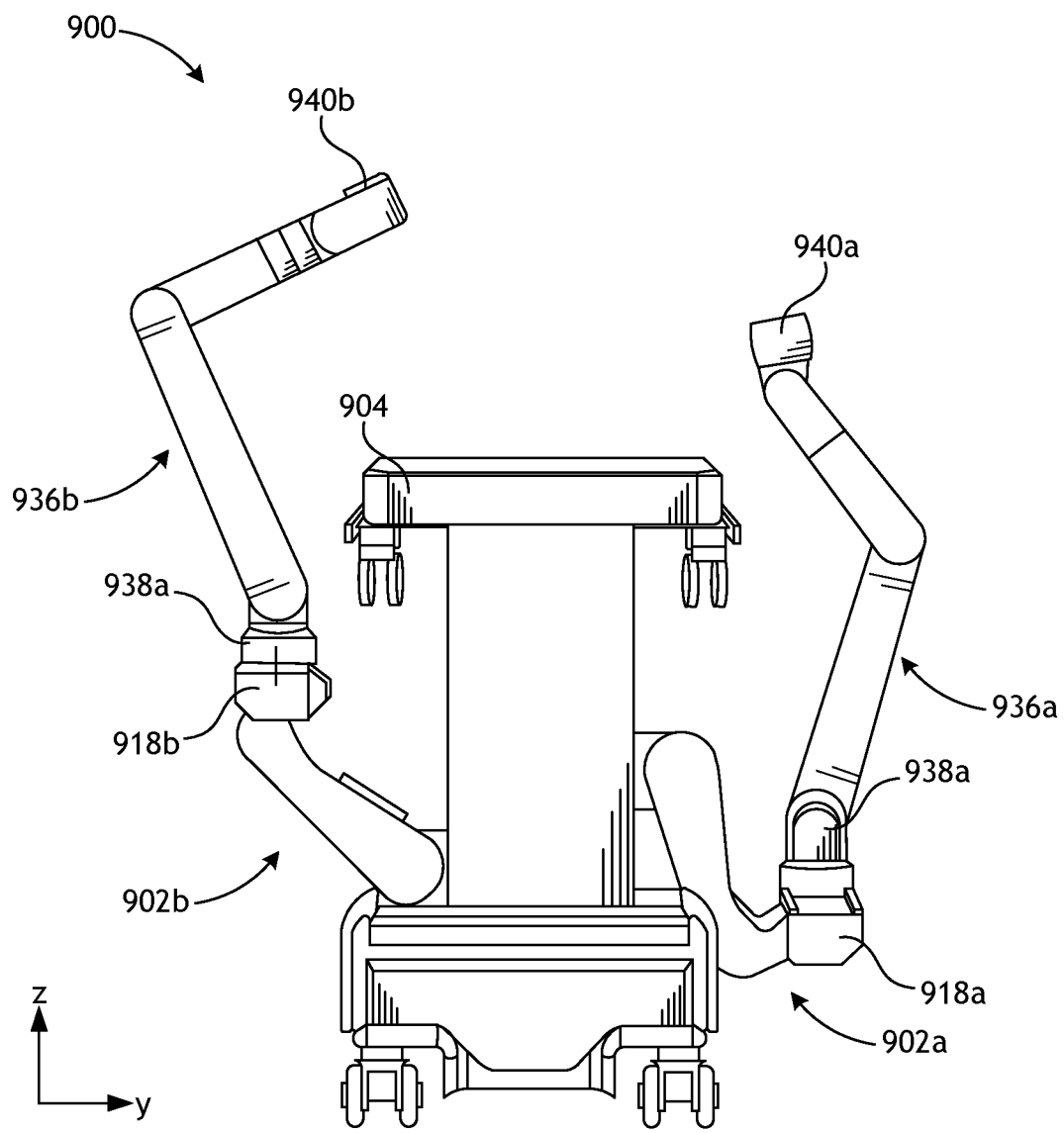
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electro-mechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
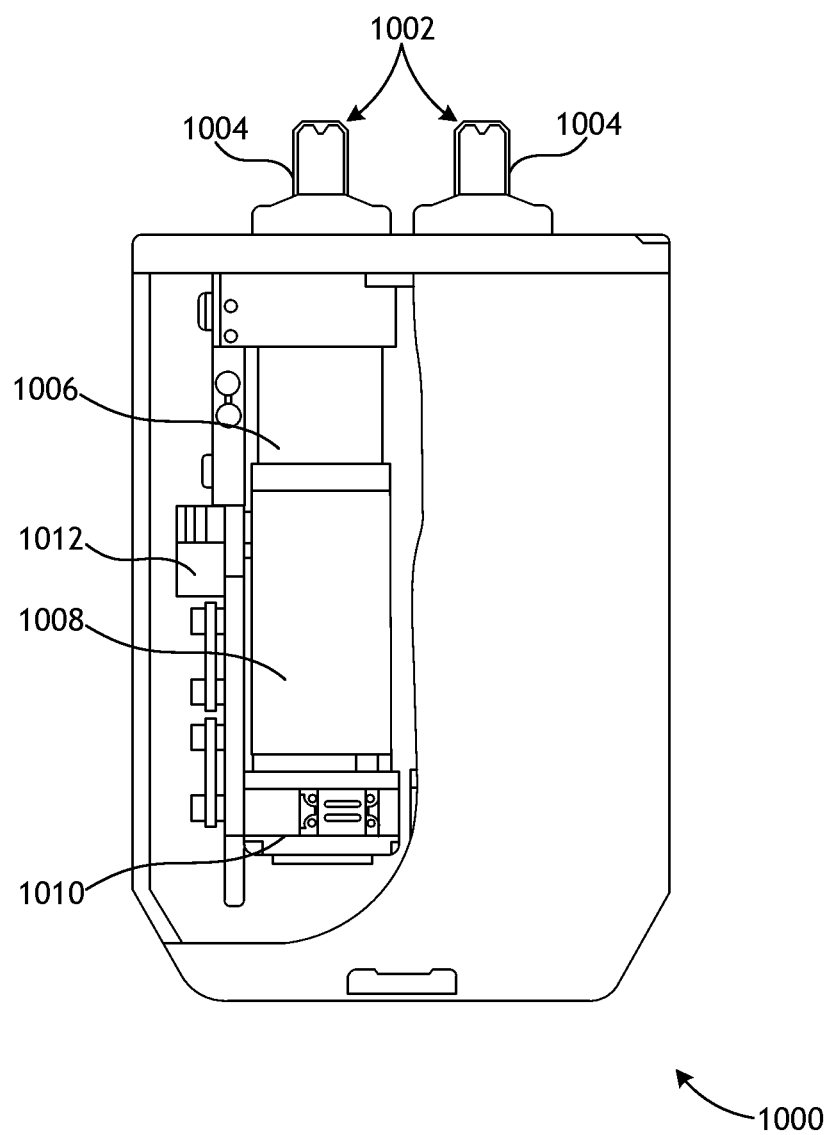
FIG. 10 illustrates an exemplary instrument driver.

FIG. 10 illustrates an example instrument driver 1000, according to one or more embodiments. Positioned at the distal end of a robotic arm, the instrument driver 1000 includes one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independently controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
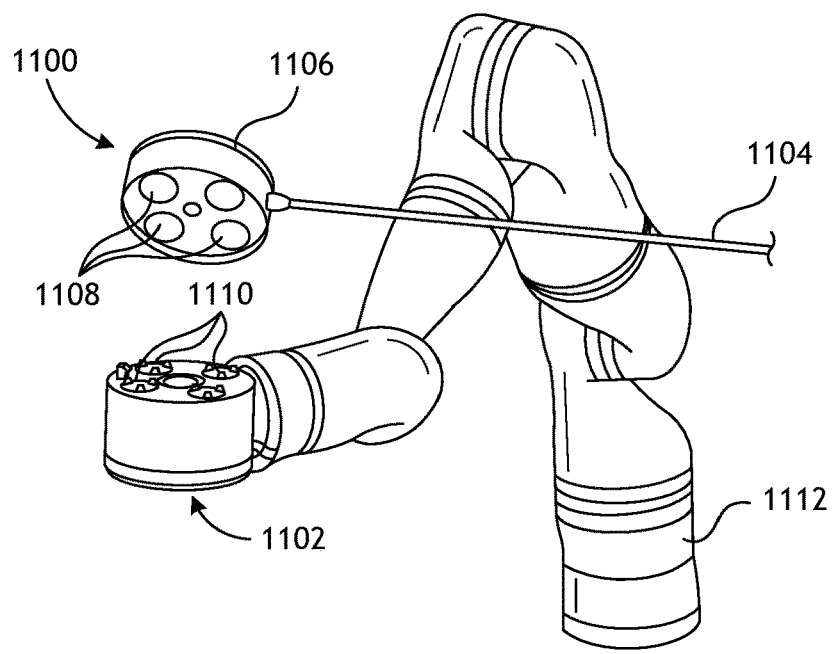
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
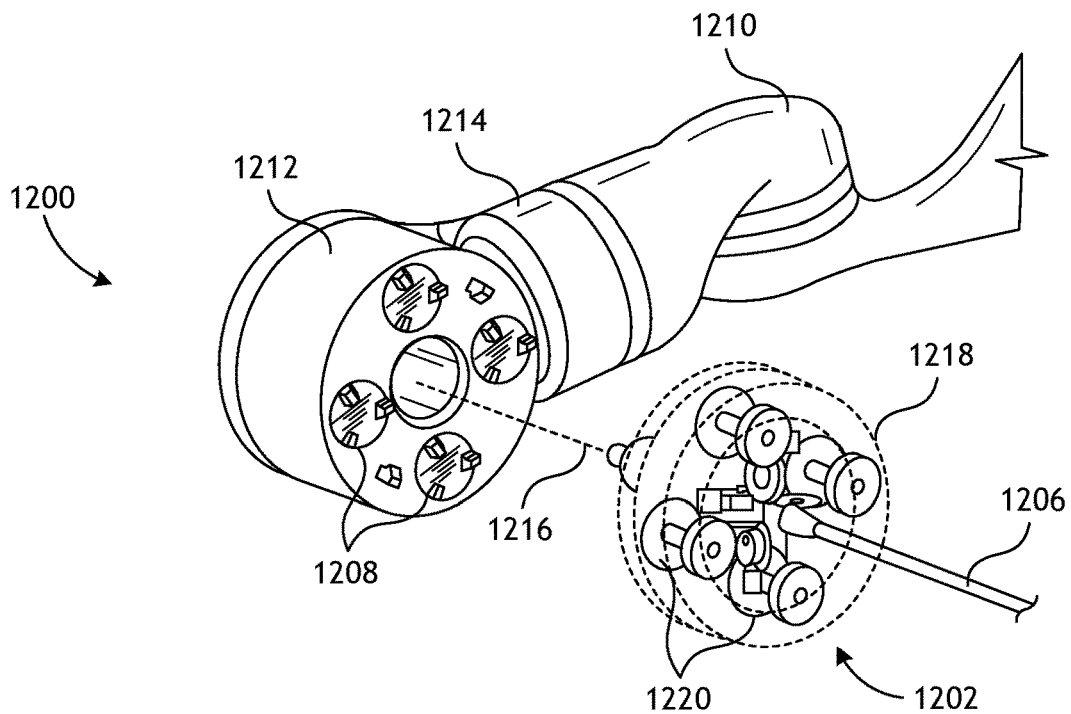
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
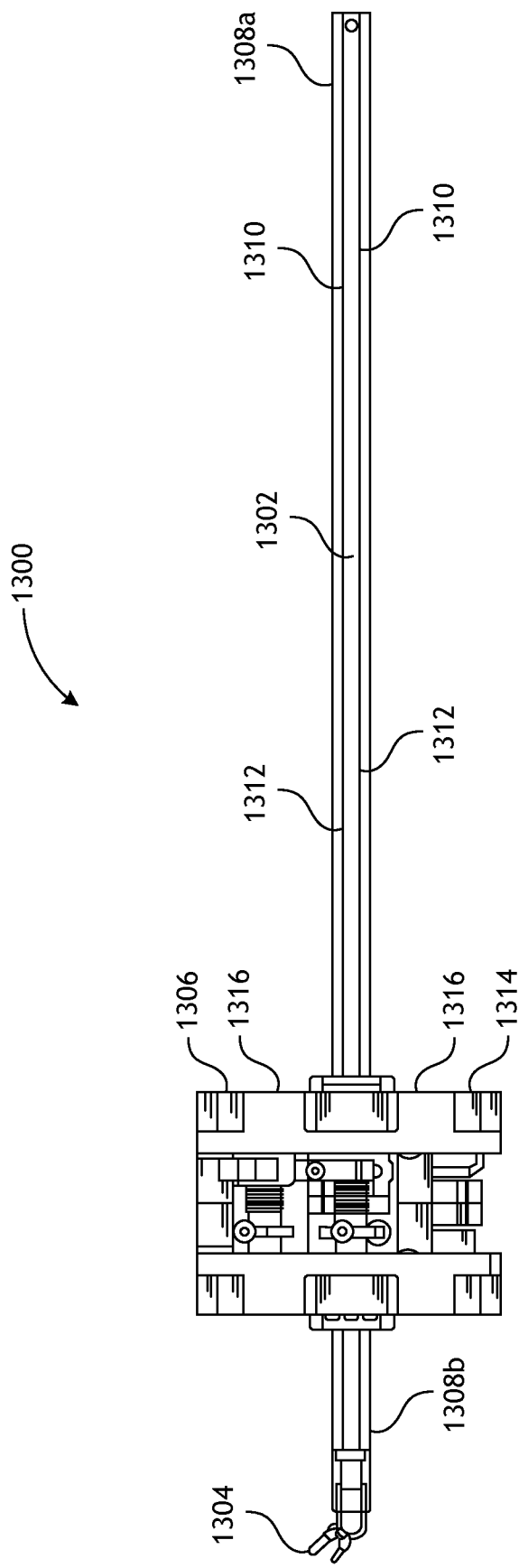
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308*a* and a distal portion 1308*b*. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument 1300, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
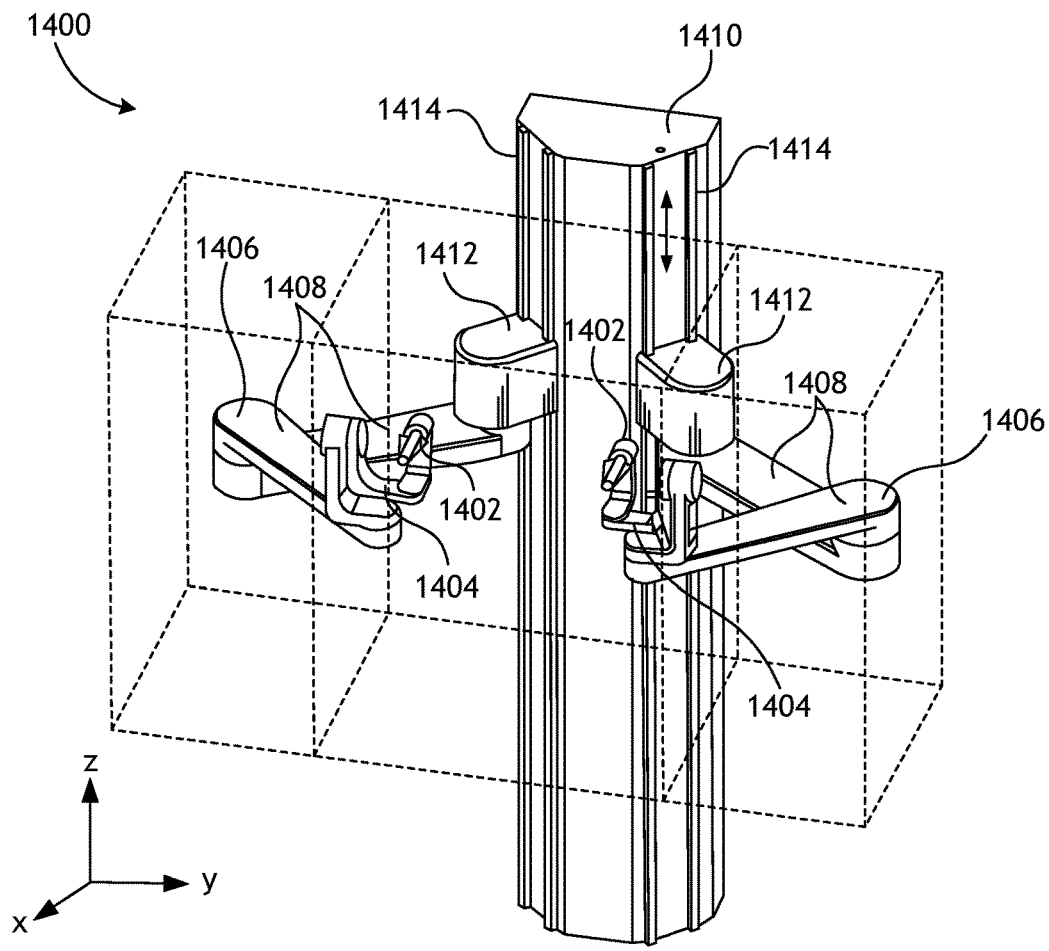
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
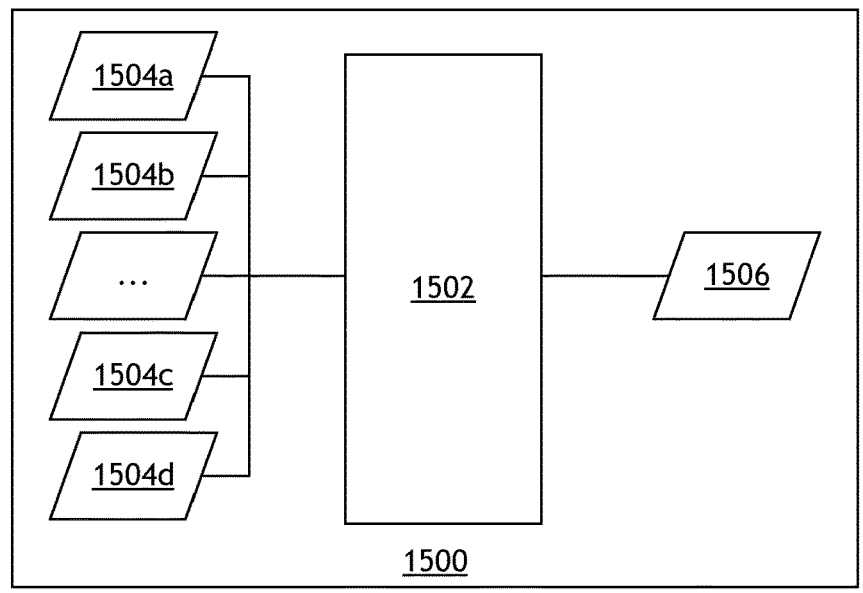
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504a, 1504b, 1504c, and 1504d to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504a-d are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504b to enable computer vision-based tracking of the medical instrument (e.g., an endoscope or an instrument advance through a working channel of the endoscope). For example, using the preoperative model data 1504a, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504a that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504b to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504c. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504*d* may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504*a-d* in combination(s). In some cases, such a combination may use a probabilistic approach where the localization module 1502 assigns a confidence weight to the location determined from each of the input data 1504*a-d*. Thus, where the EM data 1504*c* may not be reliable (as may be the case where there is EM interference) the confidence of the location determined by the EM data 1504*c* can be decrease and the localization module 1502 may rely more heavily on the vision data 1504*b* and/or the robotic command and kinematics data 1504*d*.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

Figure 16:
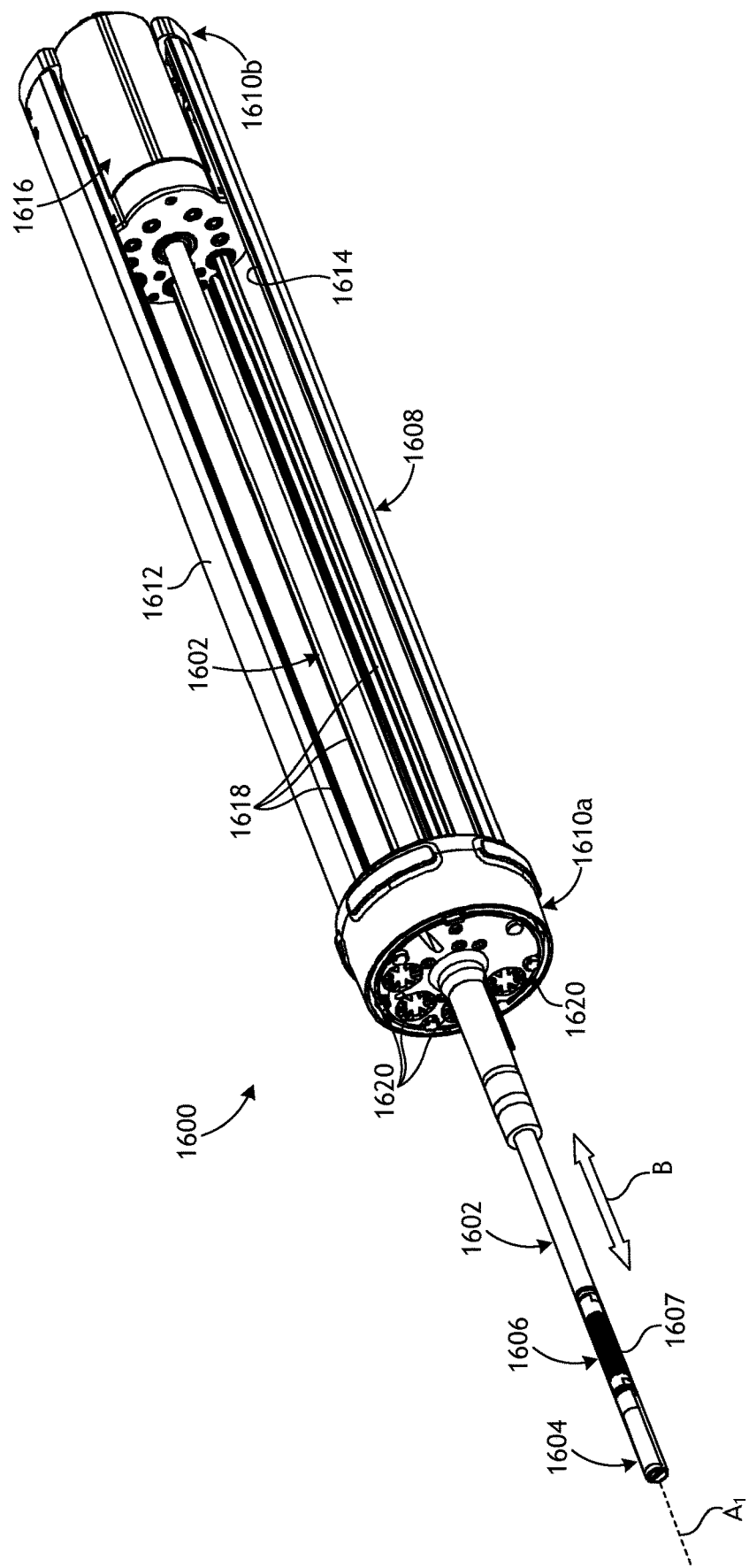
FIG. 16 is a side view of an example surgical tool that may incorporate some or all of the principles of the present disclosure.

2. Description.
Multi-Pivot, Single Degree of Freedom, Single Plane Articulation Wrist FIG. 16 is an isometric side view of an example surgical tool 1600 that may incorporate some or all of the principles of the present disclosure. The surgical tool 1600 may be similar in some respects to any of the medical instruments described above with reference to FIGS. 11-13 and, therefore, may be used in conjunction with a robotic surgical system, such as the robotically-enabled systems 100, 400, and 900 of FIGS. 1-13. As illustrated, the surgical tool 1600 includes an elongated shaft 1602, an end effector 1604 arranged at the distal end of the shaft 1602, and an articulable wrist 1606 (alternately referred to as a "wrist joint") that interposes and couples the end effector 1604 to the distal end of the shaft 1602.

The terms "proximal" and "distal" are defined herein relative to a robotic surgical system having an interface configured to mechanically and electrically couple the surgical tool 1600 to a robotic manipulator. The term "distal" refers to the position of an element closer to the end effector 1604, and thus closer to a patient and further from a robotic manipulator during operation, and the term "proximal" refers to the position of an element further away from the end effector but closer to the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a harmonic device that can be used for sealing tissue by applying radiofrequency (RF) electrosurgical energy to the tissue. In such embodiments, a transducer cable extends along (within) the shaft 1602 and terminates at the end effector 1604. In some embodiments, the transducer cable may be used for transmitting signals from visualization and sensing technology in the end effector 1604. In other embodiments, however, the transducer cable may be used to provide the necessary power for applying the RF electrosurgical energy that seals tissue.

In other embodiments, however, the principles of the present disclosure are equally applicable to other types of end effectors 1604, such as surgical instruments that include opposing jaws configured to move (actuate) between open and closed positions. In such embodiments, the end effector 1604 may comprise, but is not limited to, a surgical stapler (e.g., circular and linear staplers), a tissue grasper, surgical scissors, an advanced energy vessel sealer, a clip applier, a needle driver, a babcock including a pair of opposed grasping jaws, bipolar jaws (e.g., bipolar Maryland grasper, forceps, a fenestrated grasper, etc.), etc. In yet other embodiments, the end effector 1604 may alternatively comprise any end effector or instrument capable of being operated in conjunction with the presently disclosed robotic surgical systems and methods. Such end effectors or instruments include, but are not limited to, a suction irrigator, an endoscope (e.g., a camera), a surgical light, an energy device, an advanced visualization device (e.g., ultrasound imaging), or any combination thereof.

The wrist 1606 enables the end effector 1604 to articulate (pivot) relative to the shaft 1602 and thereby position the end effector 1604 at various desired orientations and locations relative to a surgical site. The end effector 1604 is depicted in FIG. 16 in the unarticulated position where a longitudinal axis of the end effector 1604 is substantially aligned with a longitudinal axis $A_1$ of the shaft 1602, such that the end effector 1604 is at a substantially zero angle relative to the shaft 1602. Actuating or articulating the wrist 1606 causes the end effector 1604 to transition to an articulated position, where the longitudinal axis of the end effector 1604 will be angularly offset from the longitudinal axis $A_1$ such that the end effector 1604 is oriented at a non-zero angle relative to the shaft 1602.

In the illustrated embodiment, the wrist 1606 is designed to articulate (pivot, swivel, etc.) in a single plane relative to the longitudinal axis $A_1$. In one example, for instance, the wrist 1606 may be designed to move in "pitch" (e.g., up and down) relative to the shaft 1602. However, rotating (rolling) the shaft 1602 about the longitudinal axis $A_1$ allows the wrist 1606 to alternatively move in "yaw" (e.g., left and right), or any angular orientation therebetween. In FIG. 16, a sheath 1607 is positioned over the wrist 1606, and may be made of a flexible material that allows the wrist 1606 to articulate, while simultaneously protecting the component parts of the wrist 1606 from contact with bodily fluids, etc. during operation.

Still referring to FIG. 16, the surgical tool 1600 may include a drive housing 1608 that has a first or "distal" end 1610a and a second or "proximal" end 1610b opposite the first end 1610a. As illustrated, the drive housing 1608 may include a shroud 1612 extending between the first and second ends 1610a,b. In the illustrated embodiment, the shroud 1612 comprises a tubular or cylindrical structure matable at each end with the first and second ends 1610a,b of the drive housing 1608. In some embodiments, the shroud 1612 may define a longitudinal opening or slot 1614 also extending between the first and second ends 1610a,b and exposing the interior of the shroud 1612.

A carriage 1616 is positioned within the shroud 1612 and is operable to move (translate) between the first and second ends 1610a,b along the longitudinal axis $A_1$ (e.g., z-axis translation). The shaft 1602 extends from the carriage 1616 and penetrates the first end 1610a. As the carriage 1616 axially advances or retracts within the drive housing 1608, the shaft 1602 and the end effector 1604 correspondingly advance or retract relative to the drive housing 1608, as indicated by the arrows B. The carriage 1616 houses an actuation system (not shown) designed to facilitate axial translation of the carriage 1616, articulation (movement) of the wrist 1606, and actuation (operation) of the end effector 1604.

At least two drive members (obscured in FIG. 16) extend from the carriage 1616 within the shaft 1602 and to the wrist 1606. As described in more detail below, the drive members may be referred to as "articulation bands" and may comprise generally rectangular bands of a material capable of being placed in tension and compression. Selective actuation of the drive members via the actuation system included in the carriage 1616 may cause the wrist 1616 to articulate.

In embodiments where the end effector 1604 is a harmonic device, a transducer cable (obscured in FIG. 16) may also extend from the carriage 1616 within the shaft. The transducer cable may extend through the wrist 1606 and terminate at the end effector 1604 to provide the necessary power for applying the RF electrosurgical energy that seals tissue, or otherwise transmit signals from visualization and sensing technology in the end effector 1604, as briefly mentioned above.

In embodiments where the end effector 1604 comprises a tool that includes opposing jaws, one or more additional drive members may extend from the carriage 1616 within the shaft 1602 and terminate at the end effector 1604. These additional drive members may include cables, lines, cords, wires, ropes, strings, twisted strings, or elongate members, and selective actuation of these drive members via the actuation system included in the carriage 1616 may cause the end effector 1604 to operate. Operating the end effector 1604 in such embodiments may include closing and/or opening the jaws, and thereby enabling the end effector 1604 to grasp (clamp) onto tissue. Once tissue is grasped or clamped between the opposing jaws, operating the end effector 1604 may further include "firing" the end effector 1604, which may refer to causing a cutting element or knife to advance distally to transect tissue grasped between the opposing jaws.

The first end 1610a of the drive housing 1608 may alternately be referred to as a "handle" since it is typically gripped by a user when attaching the surgical tool 1600 to an instrument driver (not shown). The drive housing 1608 provides various coupling features (not shown) configured to releasably couple the surgical tool 1600 to the instrument driver at the first end 1618a. One or more splines 1618 (three shown) extend longitudinally between the first and second ends 1610a,b. The splines 1618 are rotatably mounted to the first and second ends 1610a,b and extend through the carriage 1616. Selective rotation (actuation) of the splines 1618 acts on the actuation system within the carriage 1616 to cause various operations of the surgical tool 1600, such as articulating the wrist 1606 and moving the carriage 1618 along the longitudinal axis $A_1$ (e.g., z-axis translation). In embodiments where the end effector 1604 includes opposing jaws, actuation of one or more of the splines 1618 may also cause the end effector 1604 to operate, as generally described above.

The first end 1610a of the drive housing 1608 (i.e., the "handle") may include one or more rotatable drive inputs 1620 (four shown). While only four drive inputs 1620 are depicted, more or less than four may be included, as need requires. In the illustrated embodiment, three of the drive inputs 1620 may be actuatable to independently drive (rotate) the corresponding three splines 1618. The fourth drive input 1620 may be actuatable to operate a pulley and cable system (not shown) included in the drive housing 1608 to move the carriage 1616 distally or proximally, depending on the rotational direction of the fourth drive input 1620. Each drive input 1620 may be matable with a corresponding drive output of an instrument driver (not shown) matable with the drive housing 1608 at the first end 1610a. Movement (rotation) of a given drive output correspondingly moves (rotates) the associated drive input 1620 and thereby rotates the mated spline 1618 or pulley and cable system.

Figure 17A:
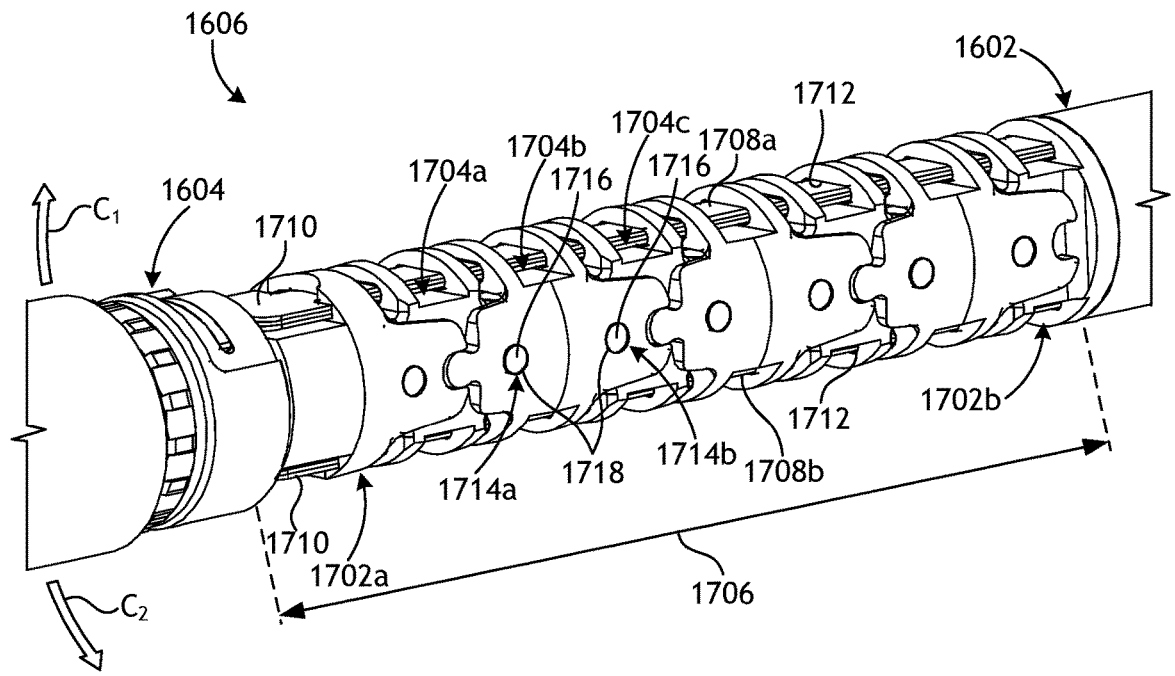
FIGS. 17A and 17B are enlarged isometric views of the articulable wrist of FIG. 16, according to one or more embodiments.
Figure 17B:
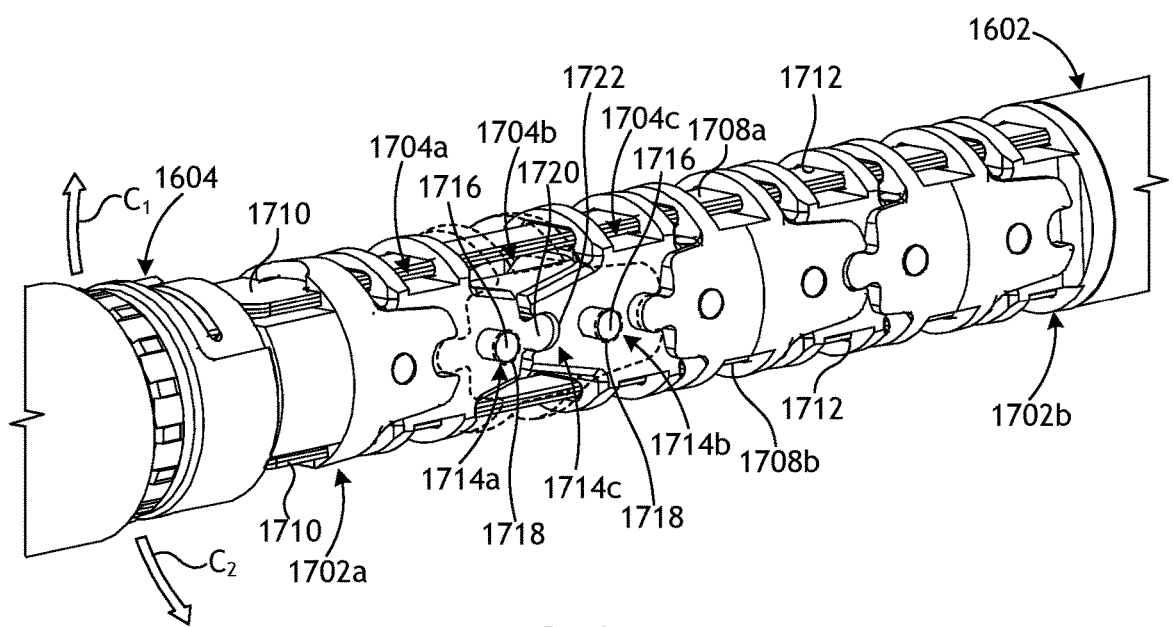

FIGS. 17A and 17B are enlarged isometric views of the articulable wrist 1606, according to one or more embodiments. The sheath 1607 (FIG. 16) is omitted in FIGS. 17A and 17B, thereby exposing at least some of the internal component parts of the wrist 1606. FIGS. 17A-17B differ only in that a small portion of the wrist 1606 in FIG. 17B is shown in phantom (dashed lines) to enable viewing of various internal features of the wrist 1606.

As illustrated, the wrist 1606 may include a distal connector 1702a, a proximal connector 1702b, and a plurality of articulation links extending between the connectors 1702a,b and shown as at least a first articulation link 1704a, a second articulation link 1704b, and a third articulation link 1704c. The distal connector 1702a may be configured to couple the wrist 1606 to the end effector 1604, and the proximal connector 1702b may be configured to couple the wrist 1606 to the distal end of the shaft 1602. The distal-most articulation link may be pivotably coupled to a proximal end of the distal connector 1702a, and the proximal-most articulation link may be pivotably coupled to a distal end of the proximal connector 1702b.

The articulation links 1704a-c are capable of being pivotably interconnected and arranged in series to extend between the distal and proximal connectors 1702a,b and otherwise along a longitudinal length 1706 (FIG. 17A) of the wrist 1606. While FIGS. 17A-17B only reference three articulation links 1704a-c for purposes of discussion, the wrist 1606 can include more than three, as illustrated. In the illustrated embodiment, the first and third articulation links 1704a,c exhibit the same design and configuration, while the second articulation link 1704b is different and axially interposes the first and third articulation links 1704a,c. As can be seen in FIGS. 17A-17B, the first and second articulation links 1704a,b are repeated in an alternating pattern along the length 1706 of the wrist 1606. Consequently, while the following discussion is directed to the three articulation links 1704a-c, it will be appreciated that the principles described herein are equally applicable to any of the articulation links that form part of the wrist 1606.

The wrist 1606 also includes one or more drive members, shown as a first drive member 1708a and a second drive member 1708b (partially visible on bottom). In the illustrated embodiment, the drive members 1708a,b are depicted in the form of generally rectangular and elongate articulation bands. Accordingly, the drive members 1708a,b will be alternately referred to herein as first and second "articulation bands" 1708a and 1708b. In other embodiments, however, the articulation bands 1708a,b may be replaced with other types of drive members, such as cables, lines, cords, wires, ropes, strings, twisted strings, or elongate members.

The articulation bands 1708a,b extend from the drive housing 1608 and, more particularly, from the carriage 1616, and selective actuation of the articulation bands 1708a,b causes articulation of the wrist 1606 in one plane of motion. In the illustrated embodiment, the articulation bands 1708a,b may be capable of being placed in both tension and compression, and thereby able to antagonistically articulate the wrist 1606. The articulation bands 1708a,b extend along the entire longitudinal length 1706 of the wrist 1606, and may each terminate at the distal connector 1702a with a connector 1710. In the illustrated embodiment, the connector 1710 comprises an enlarged head provided on each articulation band 1708a,b, but could alternatively comprise other types of connections including, but not limited to, a welded or brazed interface, an interference fit, a pinned engagement, a mechanically fastened engagement, a dovetail engagement, or any combination thereof.

The articulation bands 1708a,b may extend through portions of some or all of the articulation links 1704a-c as they extend along the longitudinal length 1706 of the wrist 1606. In some embodiments, for example, each link 1704a-c may define opposing band apertures or "lumens" 1712 provided at angularly opposite positions of each articulation link 1704a-c. In such embodiments, the articulation bands 1708a,b may be received within and otherwise extend through the band lumens 1712 of some or all of the articulation links 1704a-c. When the wrist 1606 is assembled, the band lumens 1712 of each articulation link 1704a-c may axially align such that the articulation bands 1708a,b can pass therethrough in a relatively direct course. Moreover, the articulation bands 1708a,b are not bound within the band lumens 1712, thereby allowing the articulation bands 1708a,b to axially translate relative to the articulation links 1704a-c during operation, which facilitates articulation of the wrist 1606 in at least one plane of motion.

Having the two articulation bands 1708a,b arranged on angularly opposite sides (positions) of the articulation links 1704a-c allows the articulation bands 1708a,b to antagonistically operate and thereby move the wrist 1606 in a single plane of motion. For example, providing tension (pulling) on the first articulation band 1708a and simultaneously providing compression (pushing) on the second articulation band 1708b may result in the wrist 1606 articulating in a first direction $C_1$ (e.g., "up"). In contrast, providing tension (pulling) on the second articulation band 1708b and simultaneously providing compression (pushing) on the first articulation band 1708a may result in the wrist 1606 articulating in a second direction $C_2$ (e.g., "down"), opposite the first direction $C_1$. While the directions $C_1$, $C_2$ shown in FIGS. 17A-17B depict "pitch" (e.g., up and down) movement, rotating (rolling) the shaft 1602 about the longitudinal axis $A_1$ (FIG. 16) allows the wrist 1606 to alternatively move in "yaw" (e.g., left and right) motion, or any angular orientation therebetween, as mentioned above.

As discussed in more detail herein, each articulation link 1704a-c defines a central aperture sized to receive a transducer cable extending from the carriage 1616 (FIG. 16). Consequently, when the articulation links 1704a-c are pivotably interconnected, the aligned central apertures define a central lumen that extends along the entire longitudinal length 1706 of the wrist 1606, and which allows the transducer cable to extend through the wrist 1606 to reach the end effector 1604. In other embodiments, however, the central lumen may be used to accommodate other features of the surgical tool 1600 (FIG. 16), such as, for example, a feedbar for a surgical stapler, or one or more drive members extending to the end effector 1604.

As mentioned herein, the articulation links 1704a-c can be pivotably interconnected in series along the longitudinal length 1706 to cooperatively form the wrist 1606. In particular, the first articulation link 1704a may be pivotably coupled to the second articulation link 1704b at a first coupling interface 1714a, the second articulation link 1704b may be pivotably coupled to the third articulation link 1704c at a second coupling interface 1714b, and as best seen in FIG. 17B, which shows the second articulation link 1704b in phantom (dashed lines), the first and third articulation links 1704a,c may be pivotably coupled at a third coupling interface 1714c. In some embodiments, the third coupling interface 1714c may axially interpose the first and second coupling interfaces 1714a,b. Said differently, the third coupling interface 1714c may be arranged at a position located between the first and second coupling interfaces 1714a,c along the longitudinal length 1706. This may be possible since at least a portion of the second link 1704b is arranged radially outward from the first and third links 1704a,c and is thereby able to extend over and otherwise overlap portions of the first and third links 1704a,c.

Each coupling interface 1714a-c allows each interconnected link 1704a-c to pivot (rotate) in a single plane relative to the opposing interconnected link 1704a-c. Moreover, having the first and third articulation links 1704a,c pivotably coupled at the third coupling interface 1714c located at an intermediate axial (longitudinal) location between the opposing ends of the second articulation link 1704b reduces the potential degrees of freedom at each articulation link 1704a-c. This prevents one coupling interface 1714a-c from pivoting in one angular (arc) direction while an axially (longitudinally) adjacent coupling interface 1714a-c pivots in an opposite angular (arc) direction, thus resulting in the wrist 1606 curving in two or more arcuate directions along the longitudinal length 1706. Instead, joining the first and third articulation links 1704a,c at the third coupling interface 1714c forces the wrist 1606 to articulate in a continuous arc along the longitudinal length 1706. This advantageously results in a single degree of freedom, kinematically deterministic articulation joint, which facilitates a consistent and known position of the end effector 1604 during use.

The coupling interfaces 1714a-c can assume a variety of joint mechanism designs and configurations that allow each interconnected link 1704a-c to pivot (rotate) in a single plane relative to the opposing interconnected link 1704a-c. In the illustrated embodiment, the first and third coupling interfaces 1714a,c comprise a pin and aperture joint mechanism. More specifically, the first and third articulation links 1704a,c each provide a pin 1716 sized to be received within a corresponding aperture 1718 defined by the second articulation link 1704b. Once the pins 1716 are received within the corresponding apertures 1718, pivotable movement between the interconnected links 1704a,b and 1704b,c is facilitated at the first and second coupling interfaces 1714a and 1714b. As will be appreciated, in other embodiments, the pins 1716 may alternatively be provided by the second articulation link 1704b, and the apertures 1718 may alternatively be defined by first and third articulation links 1704a,c, or any combination thereof, without departing from the scope of the disclosure.

The third coupling interface 1714c comprises a lobe and slot joint mechanism. More specifically, and as best seen in FIG. 17B, the first articulation link 1704a provides a lobe 1720 at one axial end, and the third articulation link 1704c defines a slot 1722 at an adjacent axial end and sized to receive the lobe 1720 in a sliding, pivotable engagement. Once the lobe 1720 is received within the slot 1722, pivotable movement between the first and third interconnected links 1704a,c is facilitated at the third coupling interface 1714c. As will be appreciated, in other embodiments, the lobe 1720 may alternatively be provided by the third articulation link 1704c, and the slot 1722 may be defined by the first articulation link 1704a, without departing from the scope of the disclosure. Moreover, while the third coupling interface 1714c is characterized herein as the lobe 1720 and the slot 1722 being joined in a "pivotable" relationship, the third coupling interface 1714c also facilitates a small degree of axial translation between the lobe 1720 and the slot 1722 to allow the wrist 1606 to articulate. In other words, the pivotable engagement between the lobe 1720 and the slot 1722 at the third coupling interface 1714c is not a tight pivoting engagement, but instead allows a small amount of play that allows the lobe 1720 to axially translate a small distance within the slot 1722 during articulation of the wrist 1606.

Figure 18A:
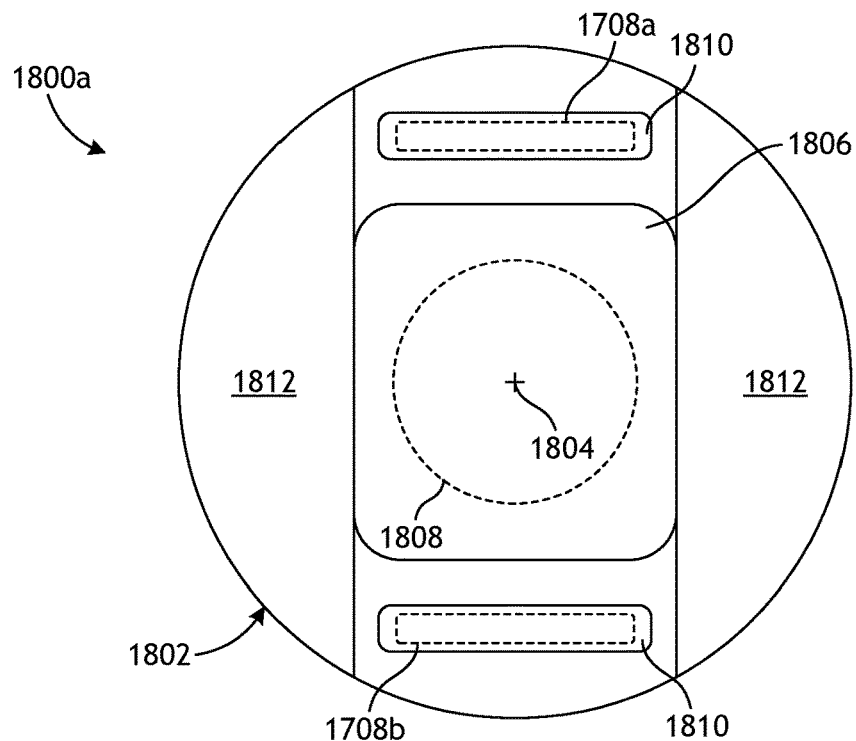
FIG. 18A is a cross-sectional end view of an example articulation link, according to one or more embodiments.

FIG. 18A is a cross-sectional end view of an example articulation link 1800a, according to one or more embodiments. The articulation link 1800a may be representative of any of the articulation links 1704a-c of FIGS. 17A-17B and, therefore, may form part of the wrist 1606 of FIGS. 16 and 17A-17B. Alternatively, the articulation link 1800a may be representative of any of the articulation links described herein.

As illustrated, the articulation link 1800a may have a generally circular body 1802 and a central axis 1804 extends through the middle (center) of the body 1802. A central aperture 1806 is defined in the body 1802 and is aligned concentrically with the central axis 1804. As briefly mentioned above, in some embodiments, the central aperture 1806 may be sized to receive a transducer cable 1808 (shown in dashed lines). When multiple articulation links 1800a are pivotably connected and arranged in series, the central aperture 1806 of each link 1800a will be aligned along the central axis 1804 and cooperatively define a central lumen extending along the entire longitudinal length 1706 (FIG. 17A) of the wrist 1606 (FIGS. 16 and 17A-17B) and through which the transducer cable 1808 can extend.

The body 1802 may further define opposing band apertures or "lumens" 1810 provided at angularly opposite positions of the body 1802. The band lumens 1810 may be the same as or similar to the band lumen 1712 of FIGS. 17A-17B and, therefore, may be configured to accommodate corresponding articulation bands 1708a,b (shown in dashed lines).

The body 1802 may further include a joint mechanism 1812 provided on opposing lateral sides of the body 1802, where each joint mechanism 1812 is 90° angularly offset from the band lumens 1810. Each joint mechanism 1812 forms part of a corresponding coupling interface, such as the coupling interfaces 1714a-c. Accordingly, each joint mechanism 1812 may assume a variety of designs and configurations that facilitate a proper coupling interface that allows interconnected, serial articulation links 1800a to pivot (rotate) in a single plane. For example, as depicted in FIGS. 17A-17B and discussed above, the joint mechanisms 1812 may comprise pin and aperture joint mechanisms or lobe and slot joint mechanisms. Other designs and configurations of the joint mechanisms 1812 are described in more detail herein.

Figure 18B:
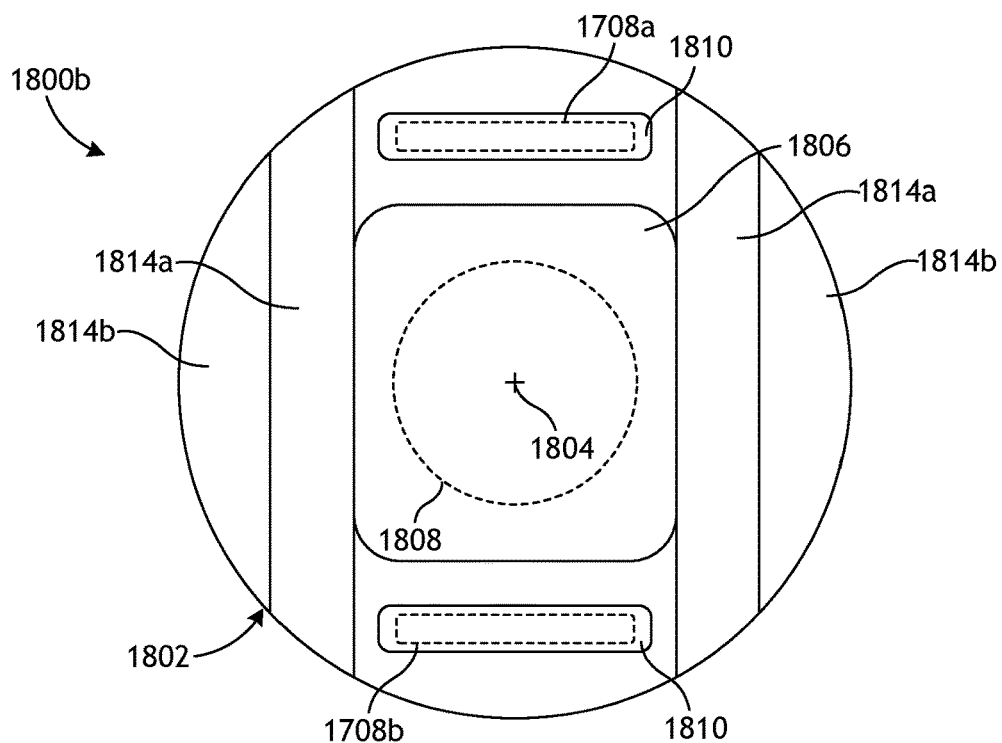
FIG. 18B is a cross-sectional end view of another example articulation link, according to one or more embodiments.

FIG. 18B is a cross-sectional end view of another example articulation link 1800b, according to one or more additional embodiments. The articulation link 1800b may be similar in some respects to the articulation link 1800a and, therefore, may be representative of any of the articulation links described herein, and may form part of the wrist 1606 of FIGS. 16 and 17A-17B, or any of the other wrists described herein. Similar to the articulation link 1800a, the articulation link 1800b may include the body 1802 that defines the central aperture 1806 aligned concentrically with the central axis 1804, where the central aperture 1806 is sized to receive the transducer cable 1808 (shown in dashed lines). Furthermore, the body 1802 includes the opposing band lumens 1810 sized to accommodate the articulation bands 1708a,b (shown in dashed lines).

The body 1802 may further provide first and second joint mechanisms 1814a and 1814b provided on each opposing lateral side of the body 1802. More specifically, in the illustrated embodiment, the second joint mechanism 1814b is spaced laterally (radially) outward from the first joint mechanism 1814a on each lateral side of the body 1802. Such an arrangement is similar to the embodiment shown in FIGS. 17A-17B where at least a portion of the second link 1704b is arranged radially outward (laterally spaced) from the first and third links 1704a,c and is thereby able to extend over and otherwise laterally overlap portions of the first and third links 1704a,c. In other embodiments, however, the second joint mechanism 1814b may be spaced laterally (radially) outward from the first joint mechanism 1814a on one lateral side of the body 1802, but spaced laterally (radially) inward from the first joint mechanism 1814a on the opposing lateral side of the body 1802, without departing from the scope of the disclosure.

Figure 19A:
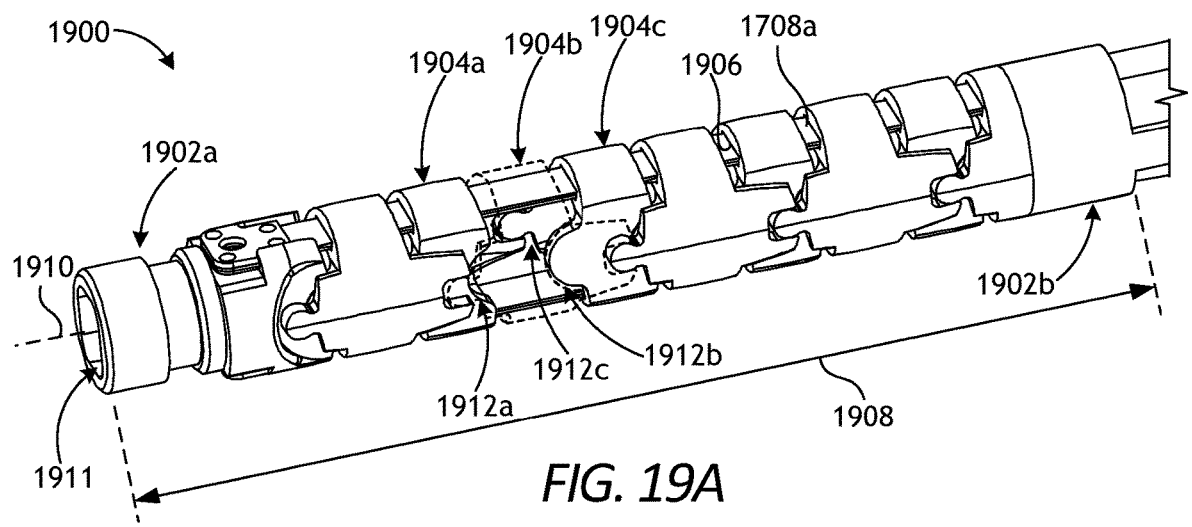
FIG. 19A is an enlarged isometric view of another example articulable wrist, according to one or more additional embodiments.

FIG. 19A is an enlarged isometric view of another example articulable wrist 1900, according to one or more embodiments. The wrist 1900 may be similar in some respects to the wrist 1606 of FIGS. 16 and 17A-17B and, therefore, may be used in the surgical tool 1600 (FIG. 16) and may otherwise replace the wrist 1606. Similar to the wrist 1606, the wrist 1900 includes distal and proximal connectors 1902a,b, and a plurality of articulation links extending between the connectors 1902a,b and shown as at least a first articulation link 1904a, a second articulation link 1904b (shown in phantom, dashed lines), and a third articulation link 1904c. The distal connector 1902a may be configured to couple the wrist 1900 to an end effector (e.g. the end effector 1604 of FIG. 16), and the proximal connector 1902b may be configured to couple the wrist 1900 to the distal end of a shaft (e.g., the shaft 1602 of FIG. 16).

The wrist 1900 also includes the first and second articulation bands 1708a,b (the second articulation band 1708b mostly occluded) extending along the entire longitudinal length of the wrist 1900 and terminating at the distal connector 1902a. The articulation bands 1708a,b may extend through portions of some or all of the articulation links 1904a-c, such as through opposing band apertures or "lumens" 1906 provided at angularly opposite positions of each articulation link 1904a-c. Operation of the wrist 1900 using the articulation bands 1708a,b is the same as or similar to operation of the wrist 1606 described above with reference to FIGS. 17A-17B and, therefore, will not be described again.

The articulation links 1904a-c are capable of being pivotably interconnected and arranged in series to extend between the distal and proximal connectors 1902a,b and otherwise along a longitudinal length 1908 of the wrist 1900. While FIG. 19A only references three articulation links 1904a-c for purposes of discussion, the wrist 1900 can include more than three, as illustrated, without departing from the scope of the disclosure. In the illustrated embodiment, the first and third articulation links 1904a,c exhibit the same design and configuration, while the second articulation link 1904b is different and axially interposes the first and third articulation links 1904a,c. Accordingly, the first and second articulation links 1904a,b are effectively repeated in an alternating pattern along the length 1908 of the wrist 1900. Consequently, while the following discussion is directed to the three articulation links 1904a-c, it will be appreciated that the principles described herein are equally applicable to any of the articulation links that form part of the wrist 1900.

When the articulation links 1904a-c are pivotably connected and arranged in series, corresponding central apertures (not shown) defined by each link 1904a-c will be aligned along a central axis 1910 of the wrist 1900 and cooperatively define a central lumen 1911 that extends along the entire longitudinal length 1908, which allows a transducer cable (not shown) to extend through the entire wrist 1900.

The articulation links 1904a-c are pivotably interconnectable in series to cooperatively form a portion of the wrist 1900. In particular, the first articulation link 1904a may be pivotably coupled to the second articulation link 1904b at a first coupling interface 1912a, the second articulation link 1904b may be pivotably coupled to the third articulation link 1904c at a second coupling interface 1912b, and the first and third articulation links 1904a,c may be pivotably coupled at a third coupling interface 1912c. In some embodiments, as illustrated, the third coupling interface 1912c may axially interpose the first and second coupling interfaces 1912a,b. Said differently, the third coupling interface 1912c may be arranged at a location between the first and second coupling interfaces 1912a,c along the longitudinal length 1908 of the wrist 1900. This may be possible since the third coupling interface 1912c is provided on the opposite angular side of the wrist 1900 as compared to the first and second coupling interfaces 1912a,b, and because the radial or lateral position of the articulation links 1904a-c stagger (alternate) along the length 1908 of the wrist 1900.

Each coupling interface 1912a-c allows each interconnected link 1904a-c to pivot (rotate) in a single plane relative to the opposing interconnected link 1904a-c. The coupling interfaces 1912a-c can assume a variety of designs and configurations to accomplish this result. Moreover, having the first and third articulation links 1904a,c pivotably coupled at the third coupling interface 1912c located at an intermediate (longitudinal) location between the opposing ends of the second articulation link 1904b reduces the potential degrees of freedom at each articulation link 1904a-c, which prevents the wrist 1900 from curving in two or more arcuate directions, but instead ensures that the wrist 1900 articulates in a continuous arc along the entire longitudinal length 1908.

FIGS. 19B-19E are exploded isometric views of the articulation links 1904a-c to enable discussion of the coupling interfaces 1912a-c, according to one or more embodiments.

Figure 19B:
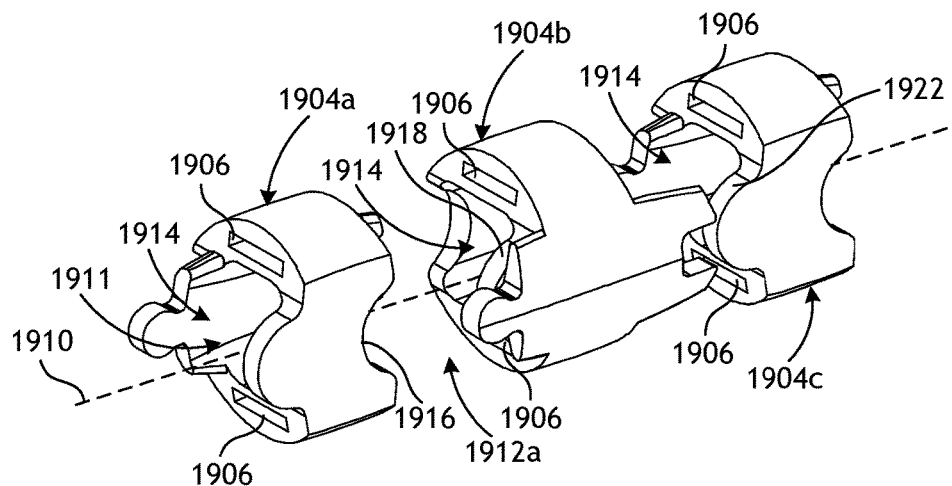
FIGS. 19B-19E are exploded isometric views of the articulation links of FIG. 19A, according to one or more embodiments.
Figure 19C:
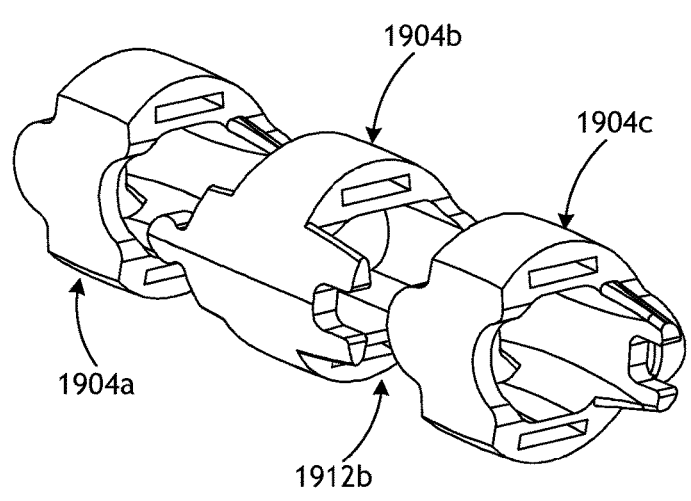

Referring first to FIG. 19B, as shown, the second articulation link 1904b generally interposes the first and third articulation links 1904a,c, and the first and third articulation links 1904a,c comprise the same structure and alternate with the second articulation link 1904b. The opposing band lumens 1906 are provided at angularly opposite positions of each articulation link 1904a-c to accommodate the first and second articulation bands 1708a,b (FIG. 19A). Moreover, each articulation link 1904a-c defines a central aperture 1914 aligned concentrically with the central axis 1910. Pivotably connecting the links 1904a-c in series along the central axis 1910 aligns the central apertures 1914 to cooperatively define the central lumen 1912, which provides a conduit for a transducer cable (e.g., the transducer cable 1808 of FIGS. 18A-18B) to extend through the entire wrist 1900 (FIG. 19A).

The first coupling interface 1912a is best seen in FIG. 19B and comprises a cam and cam surface joint mechanism. More specifically, the first articulation link 1904a defines an arcuate cam surface 1916 sized to receive a correspondingly arcuate cam 1918 provided by the second articulation link 1904b in a sliding, pivotable engagement. Once the cam 1918 is received within the cam surface 1916, pivotable movement between the first and second interconnected links 1904a,b is facilitated at the first coupling interface 1912a. As will be appreciated, in other embodiments, the cam 1918 may alternatively be provided by the first articulation link 1904a, and the cam surface 1916 may alternatively be defined by the second articulation link 1904b, without departing from the scope of the disclosure.

The second coupling interface 1912b also comprises a cam and cam surface joint mechanism. More specifically, the second articulation link 1904b provides an arcuate cam surface 1920 (FIGS. 19D and 19E) sized to be received by a correspondingly arcuate cam 1922 defined by the third articulation link 1904c (FIGS. 19B and 19D) in a sliding, pivotable engagement. Once the cam 1922 is received within the cam surface 1920, pivotable movement between the second and third interconnected links 1904b,c is facilitated at the second coupling interface 1912b. As will be appreciated, in other embodiments, the cam 1922 may alternatively be provided by the second articulation link 1904b, and the arcuate cam surface 1920 may alternatively be defined by the third articulation link 1904c, without departing from the scope of the disclosure.

Figure 19D:
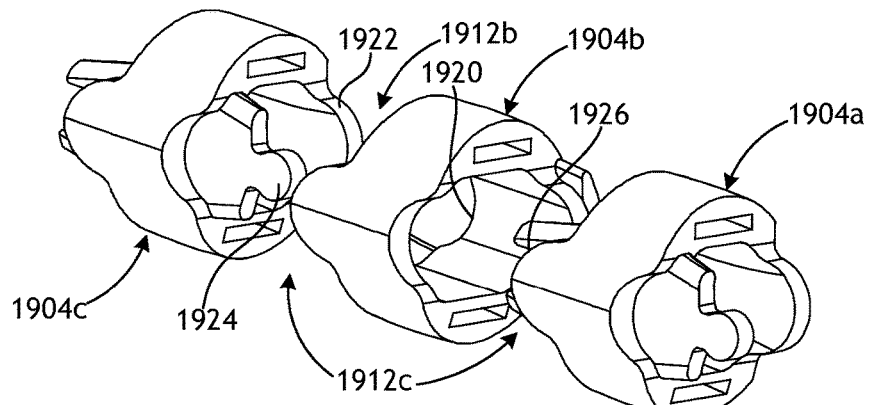
Figure 19E:
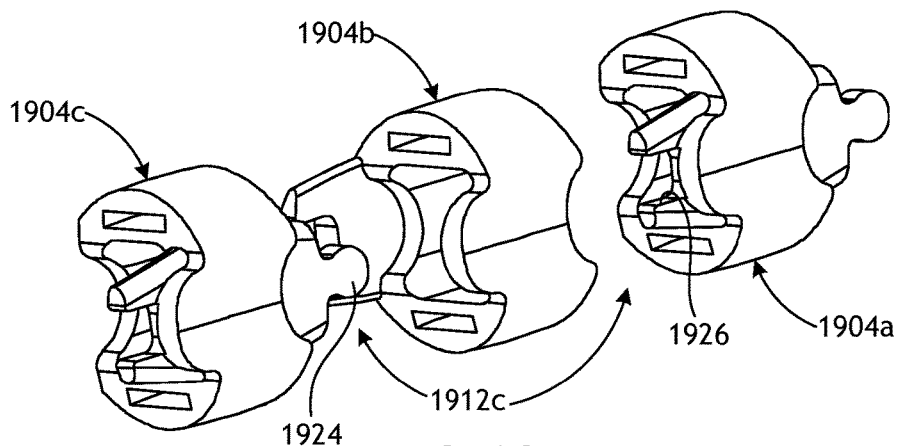

The third coupling interface 1912c comprises a lobe and slot joint mechanism. More specifically, and as best seen in FIGS. 19D and 19E, the third articulation link 1904c provides a lobe 1924 at one axial end, and the first articulation link 1904a defines a slot 1926 at an opposing axial end and sized to receive the lobe 1924 in a sliding, pivotable engagement. Once the lobe 1924 is received within the slot 1926, pivotable movement between the first and third interconnected links 1904a,c is facilitated at the third coupling interface 1912c. As will be appreciated, in other embodiments, the lobe 1924 may alternatively be provided by the first articulation link 1904a, and the slot 1926 may alternatively be defined by the third articulation link 1904c, without departing from the scope of the disclosure. While the third coupling interface 1912c is characterized herein as the lobe 1924 and the slot 1926 being joined in a "pivotable" relationship, the third coupling interface 1912c also facilitates a small degree of axial translation between the lobe 1924 and the slot 1926 to allow the wrist 1900 to articulate. In other words, the pivotable engagement between the lobe 1924 and the slot 1926 at the third coupling interface 1912c is not a tight pivoting engagement, but instead allows a small amount of play that allows the lobe 1924 to axially translate a small distance within the slot 1926 during articulation of the wrist 1900.

Referring again to FIG. 19A, the articulation links 1904a-c provide and otherwise define joint mechanisms that are arranged similar to the articulation link 1800b of FIG. 18B, where each articulation link 1904a-c provides first and second joint mechanisms provided on opposing lateral sides of the links 1904a-c. The second joint mechanisms of the links 1904a-c are spaced laterally (radially) outward from the first joint mechanisms, and this is made possible since at least a portion of the second link 1904b is spaced laterally (radially) outward from the first and third links 1904a,c and is thereby able to extend over and otherwise laterally overlap portions of the first and third links 1904a,c.

Figure 20:
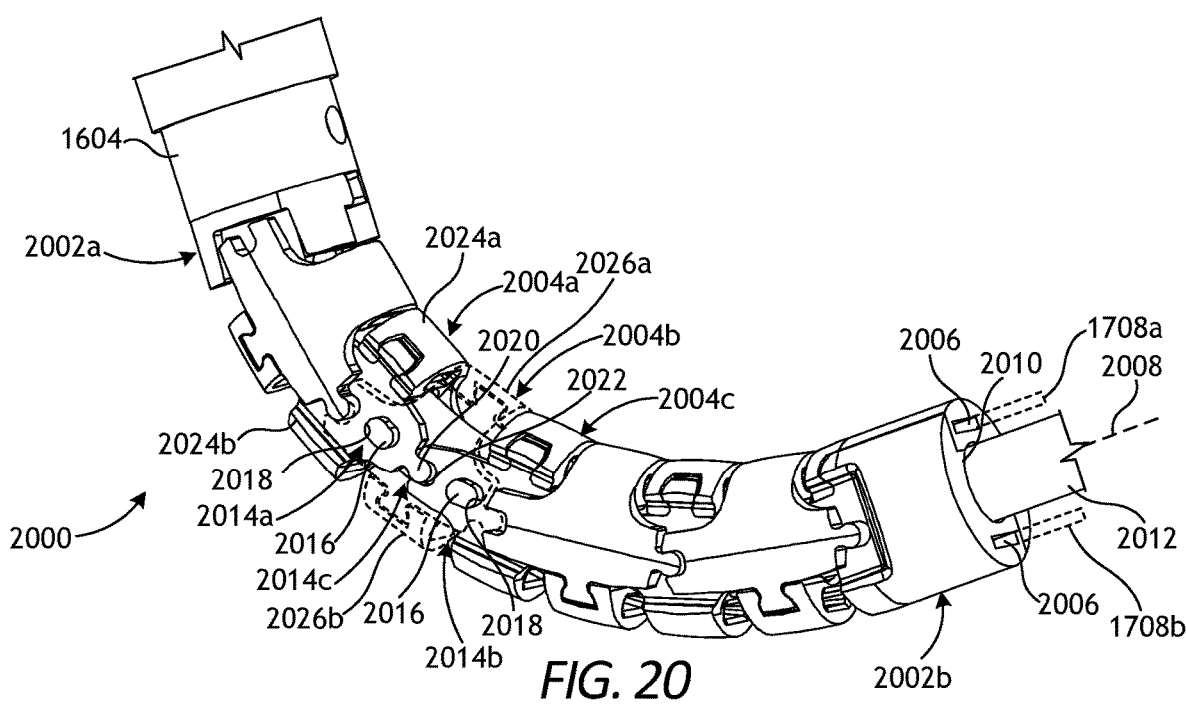
FIG. 20 is an enlarged isometric view of another example articulable wrist, according to one or more additional embodiments.

FIG. 20 is an enlarged isometric view of another example articulable wrist 2000, according to one or more additional embodiments. The wrist 2000 is shown in FIG. 20 in an articulated or curved state, and may be similar in some respects to the wrist 1606 of FIGS. 16 and 17A-17B. Accordingly, the wrist 2000 may be used in the surgical tool 1600 (FIG. 16) and may otherwise replace the wrist 1606. Similar to the wrist 1606, the wrist 2000 includes distal and proximal connectors 2002a,b, and a plurality of articulation links extending between the connectors 2002a,b and shown as at least a first articulation link 2004a, a second articulation link 2004b (shown in phantom, dashed lines), and a third articulation link 2004c. The distal connector 2002a may be configured to couple the wrist 2000 to the end effector 1604, and the proximal connector 2002b may be configured to couple the wrist 2000 to the distal end of a shaft (e.g., the shaft 1602 of FIG. 16).

The wrist 2000 can also include the first and second articulation bands 1708a,b (shown in dashed lines) extending along the entire longitudinal length of the wrist 2000 and terminating at the distal connector 2002a. The articulation bands 1708a,b may extend through portions of some or all of the articulation links 2004a-c, such as through opposing band apertures or "lumens" 2006 provided at angularly opposite positions of each articulation link 2004a-c. Operation of the wrist 2000 using the articulation bands 1708a,b is the same as or similar to operation of the wrist 1606 described above with reference to FIGS. 17A-17B and, therefore, will not be described again.

The articulation links 2004a-c are capable of being pivotably interconnected and arranged in series to extend between the distal and proximal connectors 2002a,b and otherwise along a longitudinal length of the wrist 2000. While FIG. 20 only references three articulation links 2004a-c for purposes of discussion, the wrist 2000 can include more than three, as illustrated, without departing from the scope of the disclosure. In the illustrated embodiment, the first and third articulation links 2004a,c exhibit the same design and configuration, while the second articulation link 2004b is different and axially interposes the first and third articulation links 2004a,c. Accordingly, the first and second articulation links 2004a,b are effectively repeated in an alternating (staggered) pattern along the length of the wrist 2000. Consequently, while the following discussion is directed to the three articulation links 2004a-c, it will be appreciated that the principles described herein are equally applicable to any of the articulation links that form part of the wrist 2000.

When the articulation links 2004a-c are pivotably connected and arranged in series, corresponding central apertures (not shown) defined by each link 2004a-c will be aligned along a central axis 2008 of the wrist 2000 and cooperatively define a central lumen 2010 that extends along the entire longitudinal length, which allows a transducer cable 2012 to extend through the entire wrist 2000.

The articulation links 2004a-c are pivotably interconnectable in series to cooperatively form a portion of the wrist 2000. In particular, the first articulation link 2004a may be pivotably coupled to the second articulation link 2004b at a first coupling interface 2014a, the second articulation link 2004b may be pivotably coupled to the third articulation link 2004c at a second coupling interface 2014b, and the first and third articulation links 2004a,c may be pivotably coupled at a third coupling interface 2014c. In some embodiments, as illustrated, the third coupling interface 2014c may axially interpose the first and second coupling interfaces 2014a,b. Said differently, the third coupling interface 2014c may be arranged at a location between the first and second coupling interfaces 2014a,c along the longitudinal length of the wrist 2000. This may be possible since at least a portion of the second link 2004b is arranged radially outward from the first and third links 2004a,c and is thereby able to extend over and otherwise overlap portions of the first and third links 2004a,c.

Each coupling interface 2014a-c allows each interconnected link 2004a-c to pivot (rotate) in a single plane relative to the opposing interconnected link 2004a-c. Having the first and third articulation links 2004a,c pivotably coupled at the third coupling interface 2014c located at an intermediate longitudinal location between the opposing ends of second articulation link 2004b reduces the potential degrees of freedom at each articulation link 2004a-c, which prevents the wrist 2000 from curving in two or more arcuate directions, but instead ensures that the wrist 2000 articulates in a continuous arc along the entire longitudinal length.

The coupling interfaces 2014a-c can be assume a variety of joint mechanism designs and configurations that allow each interconnected link 2004a-c to pivot (rotate) in a single plane relative to the opposing interconnected link 2004a-c. In the illustrated embodiment, the first and third coupling interfaces 2014a,c comprise a pin and pocket joint mechanism. More specifically, the first and third articulation links 2004a,c each provide a pin 2016 sized to be received within a corresponding pocket 2018 defined by the second articulation link 2004b. Each pocket 2018 defines a bottom and, therefore, does not extend entirely through the second articulation link 2004b. Once the pins 2016 are received within the corresponding pockets 2018, pivotable movement between the interconnected links 2004a,b and 2004b,c is facilitated at the first and second coupling interfaces 2014a and 2014b. As will be appreciated, in other embodiments, the pins 2016 may alternatively be provided by the second articulation link 2004b, and the pockets 2018 may alternatively be defined by first and third articulation links 2004a,c, without departing from the scope of the disclosure.

The third coupling interface 2014c comprises a lobe and slot joint mechanism. More specifically, the first articulation link 2004a provides a lobe 2020 at one axial end, and the third articulation link 2004c defines a slot 2022 at an adjacent axial end and sized to receive the lobe 2020 in a sliding, pivotable engagement. Once the lobe 2020 is received within the slot 2022, pivotable movement between the first and third interconnected links 2004a,c is facilitated at the third coupling interface 2014c. As will be appreciated, in other embodiments, the lobe 2020 may alternatively be provided by the third articulation link 2004c, and the slot 2022 may alternatively be defined by the first articulation link 2004a, without departing from the scope of the disclosure. While the third coupling interface 2014c is characterized herein as the lobe 2020 and the slot 2022 being joined in a "pivotable" relationship, the third coupling interface 2014c also facilitates a small degree of axial translation between the lobe 2020 and the slot 2022 to allow the wrist 2000 to articulate. In other words, the pivotable engagement between the lobe 2020 and the slot 2022 at the third coupling interface 2014c is not a tight pivoting engagement, but instead allows a small amount of play that allows the lobe 2020 to axially translate a small distance within the slot 2022 during articulation of the wrist 2000.

In some embodiments, one or more of the articulation links 2004a-c may be made of two or more components parts. More specifically, as illustrated, the first articulation link 2004a can comprise a first link portion 2024a and a second link portion 2024b, where the link portions 2024a,b are matable to form the articulation link 2004a. Similarly, the second articulation link 2004b can comprise a first link portion 2026a and a second link portion 2026b, where the link portions 2026a,b are matable to form the second articulation link 2004b. Having an articulation link 2004a-c made of two pieces may prove advantageous in aiding assembly around the transducer cable, in embodiments where the transducer cable has a larger end connector than is passable through the center lumen. Assembling the pieces of the articulation links 2004a-c around the transducer cable would allow for a smaller center lumen size only to allow articulation of the transducer cable, not the entire assembly. Two piece articulation links 2004a-c may also be advantageous in making a stronger linkage mechanism since the center lumen will be smaller.

Figure 21:
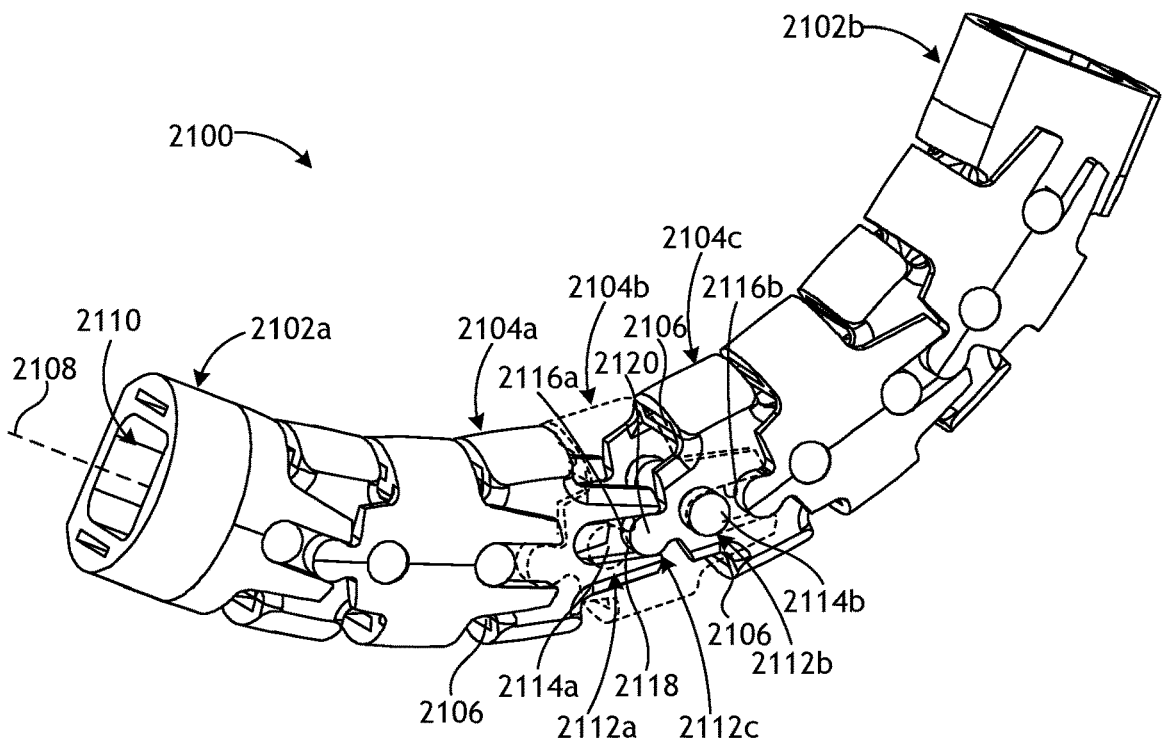
FIG. 21 is an enlarged isometric view of another example articulable wrist, according to one or more additional embodiments.

FIG. 21 is an enlarged isometric view of another example articulable wrist 2100, according to one or more embodiments. The wrist 2100 is shown in an articulated or curved state, and may be similar in some respects to the wrist 1606 of FIGS. 16 and 17A-17B and, therefore, may be used in the surgical tool 1600 (FIG. 16) and may otherwise replace the wrist 1606. As illustrated, the wrist 2100 includes distal and proximal connectors 2102a and 2102b, and a plurality of articulation links extend between the connectors 2102a,b and are shown as at least a first articulation link 2104a, a second articulation link 2104b (shown in phantom, dashed lines), and a third articulation link 2104c. The distal connector 2102a may be configured to couple the wrist 2100 to an end effector (e.g., the end effector 1604 of FIG. 16), and the proximal connector 2102b may be configured to couple the wrist 2100 to the distal end of a shaft (e.g., the shaft 1602 FIG. 16).

The wrist 2100 can also include the first and second articulation bands (not shown) extending along the longitudinal length of the wrist 2100 and terminating at or near the distal connector 2102a. The articulation bands may extend through portions of some or all of the articulation links 2104a-c, such as through opposing band lumens 2106 provided at angularly opposite positions of each articulation link 2104a-c. Operation of the wrist 2100 using the articulation bands is the same as or similar to operation of the wrist 1606 described above with reference to FIGS. 17A-17B and, therefore, will not be described again.

The articulation links 2104a-c are capable of being pivotably interconnected and arranged in series to extend between the distal and proximal connectors 2102a,b and otherwise along a longitudinal length of the wrist 2100. While FIG. 21 only references three articulation links 2104a-c for purposes of discussion, the wrist 2100 can include more than three, as illustrated, without departing from the scope of the disclosure. In the illustrated embodiment, the first and third articulation links 2104a,c exhibit the same design and configuration, while the second articulation link 2104b is different and axially interposes the first and third articulation links 2104a,c. Accordingly, the first and second articulation links 2104a,b are effectively repeated in an alternating (staggered) pattern along the length of the wrist 2100. Consequently, while the following discussion is directed to the three articulation links 2104a-c, it will be appreciated that the principles described herein are equally applicable to any of the articulation links that form part of the wrist 2100.

When the articulation links 2104a-c are pivotably connected and arranged in series, corresponding central apertures (not shown) defined by each link 2104a-c will be aligned along a central axis 2108 of the wrist 2100 and cooperatively define a central lumen 2110 that extends along the entire longitudinal length, which allows a transducer cable (not shown) to extend through the entire wrist 2100.

The articulation links 2104a-c are pivotably interconnectable in series to cooperatively form a portion of the wrist 2100. In particular, the first articulation link 2104a may be pivotably coupled to the second articulation link 2104b at a first coupling interface 2112a, the second articulation link 2104b may be pivotably coupled to the third articulation link 2104c at a second coupling interface 2112b, and the first and third articulation links 2104a,c may be pivotably coupled at a third coupling interface 2112c. In some embodiments, as illustrated, the third coupling interface 2112c may axially interpose the first and second coupling interfaces 2112a,b. Said differently, the third coupling interface 2112c may be arranged at a location between the first and second coupling interfaces 2112a,c along the longitudinal length of the wrist 2100. This may be possible since at least a portion of the second link 2104b is arranged radially (laterally) outward from the first and third links 2104a,c and is thereby able to extend over and otherwise overlap portions of the first and third links 2104a,c.

Each coupling interface 2112a-c allows each interconnected link 2104a-c to pivot (rotate) in a single plane relative to the opposing interconnected link 2104a-c. The coupling interfaces 2112a-c can assume a variety of designs and configurations to accomplish this result. Moreover, having the first and third articulation links 2104a,c pivotably coupled at the third coupling interface 2112c located at an intermediate longitudinal location between the opposing ends of the second articulation link 2104b reduces the potential degrees of freedom at each articulation link 2104a-c, which prevents the wrist 2100 from curving in two or more arcuate directions, but instead ensures that the wrist 2100 articulates in a continuous arc along the entire longitudinal length.

In the illustrated embodiment, the first coupling interface 2112a comprises a pin and slot aperture joint mechanism. More specifically, the first coupling interface 2112a includes a first pin 2114*a* sized to be received within a first slot 2116*a* defined by the first articulation link 2104*a* and further sized to extend into and be received within an aperture 2118 defined by the second articulation link 2104*b*. Once the pin 2114*a* is received within the slot 2116*a* and the aperture 2118, pivotable movement between the interconnected links 2104*a,b* is facilitated at the first coupling interface 2112*a*. In other embodiments, the slot 2116*a* may alternatively be provided by the second articulation link 2104*b*, and the aperture 2118 may be defined by first articulation link 2104*a*, without departing from the scope of the disclosure.

The second coupling interface 2112*b* comprises a pin and slot joint mechanism. More specifically, the third articulation link 2104*c* provides a second pin 2114*b* sized to be received within a second slot 2116*b* defined by the second articulation link 2104*b*. Once the pin 2114*b* is received within the slot 2116*b*, pivotable movement between the interconnected links 2104*b,c* is facilitated at the second coupling interface 2112*b*. As will be appreciated, in other embodiments, the second pin 2114*b* may alternatively be provided by the second articulation link 2104*b*, and the slot 2116*b* may be defined by third articulation link 2104*c*, without departing from the scope of the disclosure.

The third coupling interface 2112*c* comprises a lobe and slot joint mechanism. More specifically, the first articulation link 2104*a* defines the first slot 2116*a* at one axial end, as mentioned above, and the third articulation link 2104*c* provides a lobe 2120 at an adjacent axial end and sized to be received within the first slot 2116*a* in a sliding, pivotable engagement. Once the lobe 2120 is revived within the first slot 2116*a*, pivotable movement between the first and third interconnected links 2104*a,c* is facilitated at the third coupling interface 2112*c*. As will be appreciated, in other embodiments, the first slot 2116*a* may alternatively be provided by the third articulation link 2104*c*, and the lobe 2120 may alternatively be defined by the first articulation link 2104*a*, without departing from the scope of the disclosure. While the third coupling interface 2112*c* is characterized herein as the lobe 2120 and the slot 2116*a* being joined in a "pivotable" relationship, the third coupling interface 2112*c* also facilitates a small degree of axial translation between the lobe 2120 and the slot 2116*a* to allow the wrist 2100 to articulate. In other words, the pivotable engagement between the lobe 2120 and the slot 2116*a* at the third coupling interface 2112*c* is not a tight pivoting engagement, but instead allows a small amount of play that allows the lobe 2120 to axially translate a small distance within the slot 2116*a* during articulation of the wrist 2100.

Figure 22:
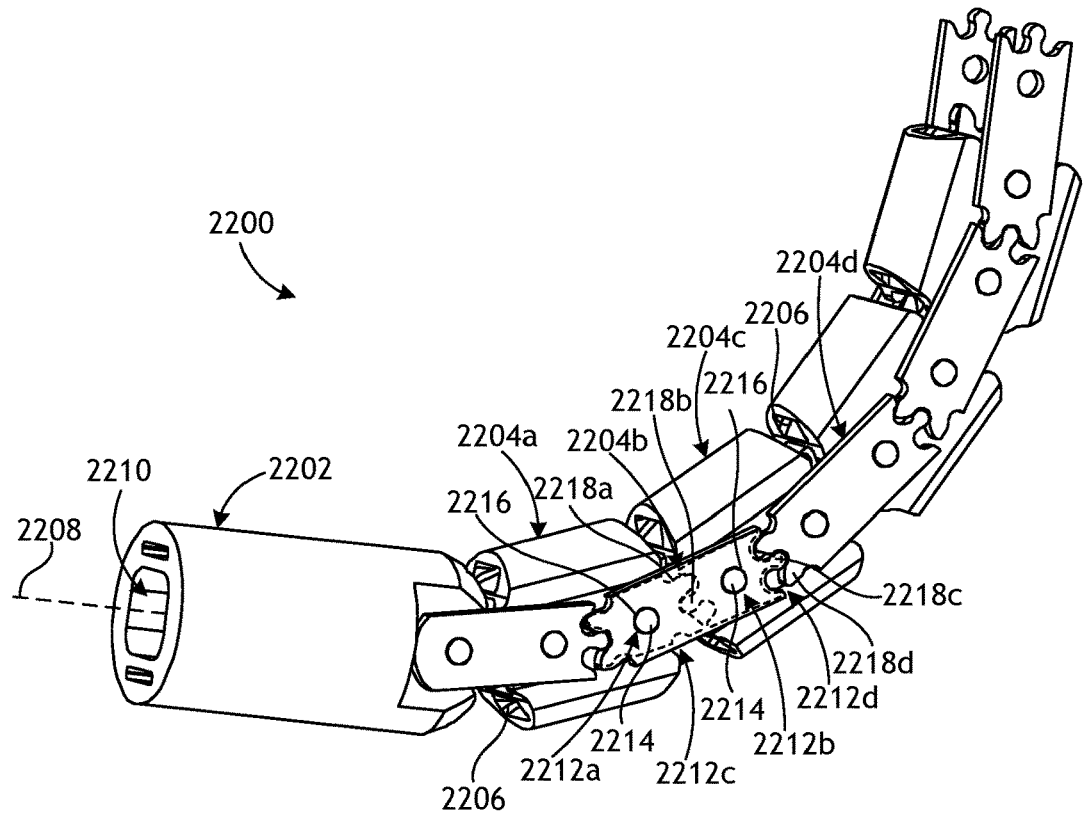
FIG. 22 is an enlarged isometric view of another example articulable wrist, according to one or more additional embodiments.

FIG. 22 is an enlarged isometric view of another example articulable wrist 2200, according to one or more additional embodiments. The wrist 2200 is shown in FIG. 22 in an articulated or curved state, and may be similar in some respects to the wrist 1606 of FIGS. 16 and 17A-17B and, therefore, may be used in the surgical tool 1600 (FIG. 16) and may otherwise replace the wrist 1606. The wrist 2200 can include a distal connector 2202 configured to couple the wrist 2200 to the end effector 1604 (FIG. 16). While not shown, the wrist 2200 may also include a proximal connector at its proximal end.

The wrist 2200 includes a plurality of articulation links extending from the distal connector 2202 and shown as at least a first articulation link 2204*a*, a second articulation link 2204*b* (shown in phantom, dashed lines), and a third articulation link 2204*c*.

The wrist 2200 can also include the first and second articulation bands (not shown) extending along the longitudinal length of the wrist 2200. The articulation bands may extend through portions of some or all of the articulation links 2204*a-c*, such as through opposing band lumens 2206 provided at angularly opposite positions of each articulation link 2204*a-c*. Operation of the wrist 2200 using the articulation bands is the same as or similar to operation of the wrist 1606 described above with reference to FIGS. 17A-17B and, therefore, will not be described again.

The articulation links 2204*a-c* are capable of being pivotably interconnected along a longitudinal length of the wrist 2200. While FIG. 22 only references three articulation links 2204*a-c* for purposes of discussion, the wrist 2200 can include more than three, as illustrated, without departing from the scope of the disclosure. In the illustrated embodiment, the first and third articulation links 2204*a,c* are the same component part and are arranged in series along the length of the wrist 2200. In contrast, the second articulation link 2204*b* comprises a plate or side member that extends along the lateral sides of the first and third articulation links 2204*a,c*. In contrast to prior embodiments, in the present embodiment, the band lumens 2206 are only provided on every other articulation link 2204*a-c* since the plates that form the second articulation link 2204*b* do not cross the radial position of the band lumens 2206. The first and second articulation links 2204*a,b* are effectively repeated in an alternating (staggered) pattern along the length of the wrist 2200. Consequently, while the following discussion is directed to the three articulation links 2204*a-c*, it will be appreciated that the principles described herein are equally applicable to any of the articulation links that form part of the wrist 2100.

When the articulation links 2204*a-c* are pivotably connected, corresponding central apertures (not shown) defined by at least the first and third links 2204*a,c* will be aligned along a central axis 2208 of the wrist 2200 and cooperatively define a central lumen 2210 that extends along the longitudinal length of the wrist 2200, which allows a transducer cable (not shown) to extend through the entire wrist 2200.

The first articulation link 2204*a* may be pivotably coupled to the second articulation link 2204*b* at a first coupling interface 2212*a*, the second articulation link 2204*b* may be pivotably coupled to the third articulation link 2204*c* at a second coupling interface 2212*b*, and the first and third articulation links 2204*a,c* may be pivotably coupled at a third coupling interface 2212*c*. In some embodiments, as illustrated, the third coupling interface 2212*c* may axially interpose the first and second coupling interfaces 2212*a,b*. Said differently, the third coupling interface 2212*c* may be arranged at a location between the first and second coupling interfaces 2212*a,c* along the longitudinal length of the wrist 2200. This may be possible since the second link 2204*b* is arranged radially (laterally) outward from the first and third links 2204*a,c* and thereby extends over and otherwise overlaps lateral portions of the first and third links 2204*a,c*.

Each coupling interface 2212*a-c* allows each interconnected link 2204*a-c* to pivot (rotate) in a single plane relative to the opposing interconnected link 2204*a-c*. Having the first and third articulation links 2204*a,c* pivotably coupled at the third coupling interface 2212*c* located at an intermediate longitudinal location between the opposing ends of the second articulation link 2204*b* reduces the potential degrees of freedom at each articulation link 2204*a-c*, which prevents the wrist 2200 from curving in two or more arcuate directions, but instead ensures that the wrist 2200 articulates in a continuous arc along the entire longitudinal length.

The coupling interfaces 2212*a-c* can be provided in a variety of joint mechanism designs and configurations that allow each interconnected link 2204*a-c* to pivot (rotate) in a single plane relative to the opposing interconnected link 2204a-c. In the illustrated embodiment, the first and second coupling interfaces 2212a,b comprise pin and aperture joint mechanisms. More specifically, the first and third articulation links 2204a,c each provide a pin 2214 sized to be received within corresponding apertures 2216 defined by the second articulation link 2204b. Once the pins 2214 are received within the corresponding apertures 2216, pivotable movement between the interconnected links 2204a,b and 2204b,c is facilitated at the first and second coupling interfaces 2212a and 2212b. As will be appreciated, in other embodiments, the pins 2214 may alternatively be provided by the second articulation link 2204b, and the apertures 2216 may alternatively be defined by first and third articulation links 2204a,c, or any combination thereof, without departing from the scope of the disclosure.

The third coupling interface 2212c comprises a geared interface joint mechanism. More specifically, a first gear profile 2218a is provided on one axial end of the first articulation link 2204a and is arranged to intermesh with a second gear profile 2218b provided on an opposing axial end of the third articulation link 2204c. The gear profiles 2218a,b may comprise, for example, cycloidal gear tooth profiles, involute gear teeth profiles, or the like. Once the gear profiles 2218a,b are intermeshed, pivotable movement between the interconnected links 2204a,c is facilitated at the third coupling interface 2212c.

In some embodiments, the second articulation link 2204b may be interconnected in series with a fourth articulation link 2204d, which be the same component part as the second articulation link 2204b, and the second and fourth articulation links 2204b,d may be arranged in series along the lateral sides of the inner articulation links 2204a,c. The second and fourth articulation links 2204b,d may be pivotably interconnected at a fourth coupling interface 2212d, which may comprise a geared interface joint mechanism. More specifically, a third gear profile 2218c is provided on one axial end of the second articulation link 2204b and is arranged to intermesh with a fourth gear profile 2218d provided on an opposing axial end of the fourth articulation link 2204d. The gear profiles 2218c,d may comprise, for example, cycloidal gear tooth profiles, involute gear teeth profiles, or the like. Once the gear profiles 2218c,d are intermeshed, pivotable movement between the interconnected links 2204b,d is facilitated at the fourth coupling interface 2212d.

Figure 23A:
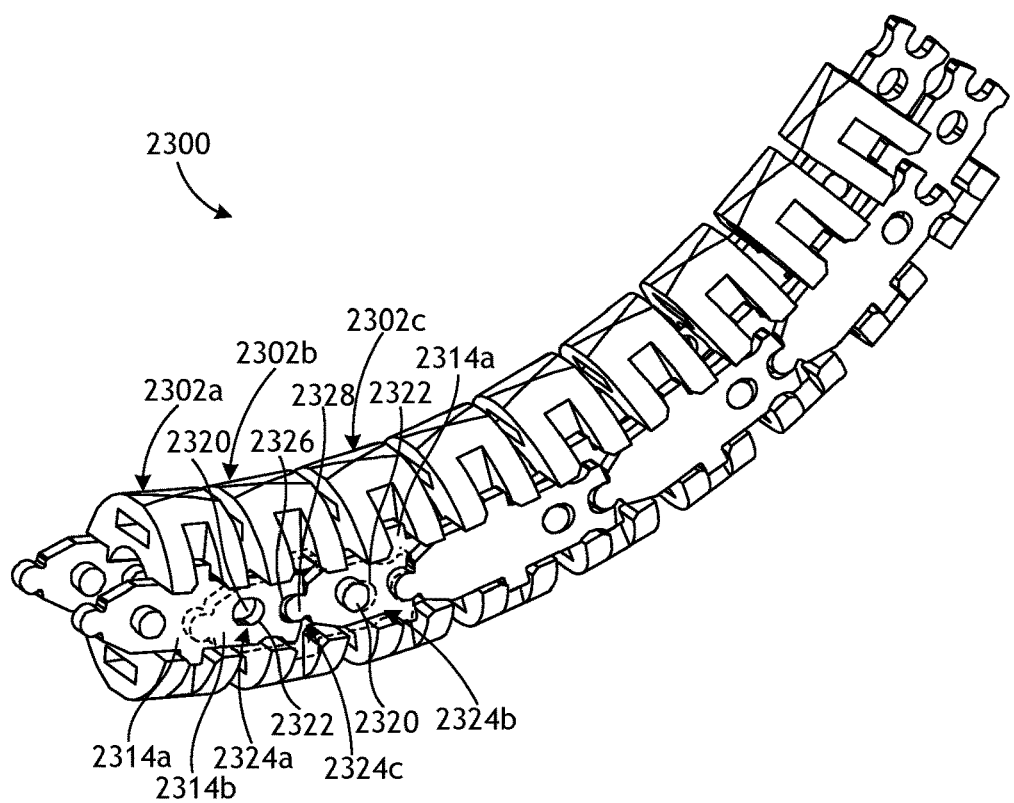
FIG. 23A is an enlarged isometric view of another example articulable wrist, according to one or more additional embodiments.

FIG. 23A is an enlarged isometric view of another example articulable wrist 2300, according to one or more additional embodiments. The wrist 2300 is shown in an articulated or curved state, and may be similar in some respects to the wrist 1606 of FIGS. 16 and 17A-17B and, therefore, may be used in the surgical tool 1600 (FIG. 16) and may otherwise replace the wrist 1606.

The wrist 2300 includes a plurality of articulation links, shown as at least a first articulation link 2302a, a second articulation link 2302b (shown in phantom, dashed lines), and a third articulation link 2302c. The articulation links 2302a-c are capable of being pivotably interconnected along a longitudinal length of the wrist 2300. While FIG. 23A only references three articulation links 2302a-c for purposes of discussion, the wrist 2300 can include more than three, as illustrated, without departing from the scope of the disclosure. In the illustrated embodiment, the articulation links 2302a-c each exhibit the same design and configuration and are, therefore, essentially the same structure pivotably interconnected in series along the length of the wrist 2300.

Figure 23B:
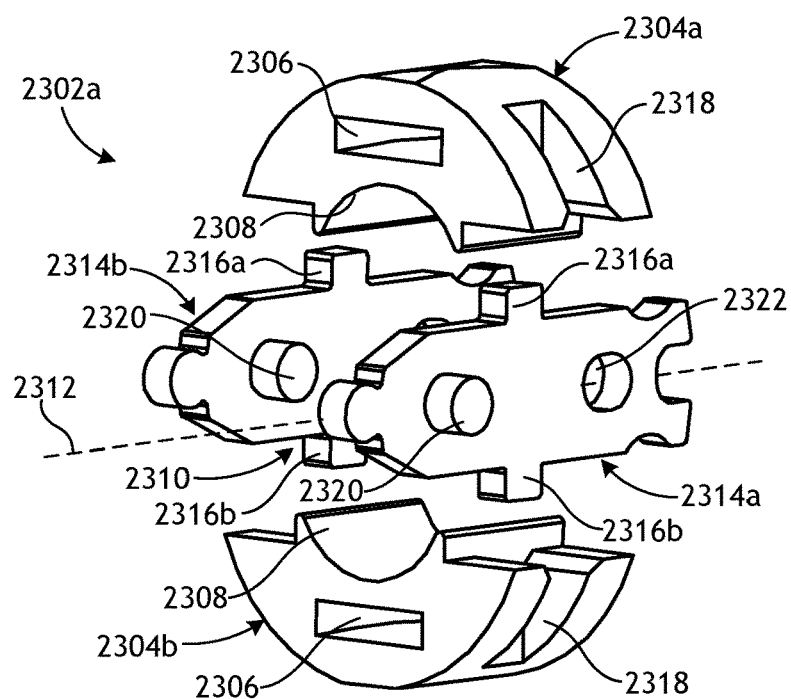
FIG. 23B is an exploded, isometric view of the first articulation link of FIG. 23A, according to one or more embodiments.

FIG. 23B is an exploded, isometric view of the first articulation link 2302a, according to one or more embodiments. The first articulation link 2302a may be representative of the second and third articulation links 2302b,c, and any of the remaining links included in the wrist 2300 (FIG. 23A). As illustrated, the link 2302a includes opposing upper and lower link portions 2304a and 2304b. Each link portion 2304a,b defines a band lumen 2306 sized to receive first and second articulation bands (e.g., articulation bands 1708a,b of FIGS. 17A-17B).

Each link portion 2304a,b also defines an inner arcuate surface 2308. When the link 2302a is assembled, the inner arcuate surfaces 2308 may help define a central aperture 2310 defined along a central axis 2312. Moreover, pivotably interconnecting the link 2302a with the other links of the wrist 2300 (FIG. 23A) will cooperatively define a central lumen that extends along the longitudinal length of the wrist 2300, which allows a transducer cable (not shown) to extend through the entire wrist 2300.

The link 2302a further includes a first side plate 2314a and a second side plate 2314b. Each side plate 2314a,b defines upper and lower tabs 2316a,b configured to mate with corresponding channels 2318 defined in the upper and lower link portions 2304a,b, respectively. Receiving the tabs 2316a,b in the corresponding channels 2318 helps axially secure the side plates 2314a,b to the link portions 2304a,b. Moreover, each side plate 2314a,b defines a pin 2320 and an aperture 2322. In at least one embodiment, the pins 2320 and the apertures 2322 may be provided at or near opposite ends of the corresponding side plates 2314a,b.

Referring again to FIG. 23A, the first articulation link 2302a may be pivotably coupled to the second articulation link 2302b at a first coupling interface 2324a, the second articulation link 2302b may be pivotably coupled to the third articulation link 2302c at a second coupling interface 2324b, and the first and third articulation links 2302a,c may be pivotably coupled at a third coupling interface 2324c. In some embodiments, as illustrated, the third coupling interface 2324c may axially (longitudinally) interpose the first and second coupling interfaces 2324a,b. Said differently, the third coupling interface 2324c may be arranged at a location between the first and second coupling interfaces 2324a,c along the longitudinal length of the wrist 2300. This may be possible since a portion of the second link 2302b is arranged radially (laterally) outward from portions of the first and third links 2302a,c and can thereby extend over and otherwise overlaps lateral portions of the first and third links 2302a,c.

Each coupling interface 2324a-c allows each interconnected link 2302a-c to pivot (rotate) in a single plane relative to the opposing interconnected link 2302a-c. Having the first and third articulation links 2302a,c pivotably coupled at the third coupling interface 2324c located at an intermediate longitudinal location between the opposing ends of the second articulation link 2302b reduces the potential degrees of freedom at each articulation link 2302a-c, which prevents the wrist 2300 from curving in two or more arcuate directions, but instead ensures that the wrist 2300 articulates in a continuous arc along the entire longitudinal length.

The coupling interfaces 2324a-c can be provided in a variety of joint mechanism designs and configurations that allow each interconnected link 2302a-c to pivot (rotate) in a single plane relative to the opposing interconnected link 2302a-c. In the illustrated embodiment, the first and second coupling interfaces 2324a,b comprise pin and aperture joint mechanisms. More specifically, the first side plate 2314a of the first articulation link 2302a defines an aperture 2322, and a second side plate 2314b of the second articulation link 2302b provides a pin 2320 sized to be received within the aperture 2322 of the first side plate 2314a of the first articulation link 2302a. The second side plate 2314b is arranged laterally (radially) outward from the first side plate 2314a. Similarly, the first side plate 2314a of the third articulation link 2302b provides a pin 2320 sized to be received within an aperture 2322 defined in the second side plate 2314b of the second articulation link 2302b. Once the pins 2320 are received within the corresponding apertures 2322, pivotable movement between the interconnected links 2302a,b and 2302b,c is facilitated at the first and second coupling interfaces 2324a and 2324b.

The third coupling interface 2324c comprises a lobe and slot joint mechanism. More specifically, the first side plate 2314a of the first articulation link 2302a defines a slot 2326 at one axial end, and the first side plate 2314a of the third articulation link 2302c provides a lobe 2328 at an adjacent axial end and sized to be received within the slot 2326 in a sliding, pivotable engagement. Once the lobe 2328 is revived within the slot 2326, pivotable movement between the first and third interconnected links 2302a,c is facilitated at the third coupling interface 2112c. As will be appreciated, in other embodiments, the slot 2326 may alternatively be provided by the third articulation link 2302c, and the lobe 2328 may alternatively be defined by the first articulation link 2302a, without departing from the scope of the disclosure. While the third coupling interface 2324c is characterized herein as the lobe 2328 and the slot 2326 being joined in a "pivotable" relationship, the third coupling interface 2324c also facilitates a small degree of axial translation between the lobe 2328 and the slot 2326 to allow the wrist 2300 to articulate. In other words, the pivotable engagement between the lobe 2328 and the slot 2326 at the third coupling interface 2324c is not a tight pivoting engagement, but instead allows a small amount of play that allows the lobe 2328 to axially translate a small distance within the slot 2326 during articulation of the wrist 2300.

Accordingly, in the illustrated embodiment, the side plates 2314a,b of each link 2302a-c are arranged to interact with axially adjacent side plates 2314a,b of succeeding or preceding links 2302a-c. The first side plates 2314a of the first and third link 2302a,c, for example, may be arranged laterally inward (e.g., toward the central axis 2312 of FIG. 23) as compared to the second side plate 2314b of the first link 2302b. On the opposing lateral side of the wrist 2300, however, the second side plates 2314b of the first and third links 2302a,c may be arranged laterally outward (e.g., away from the central axis 2312 of FIG. 23) as compared to the second side plate 2314b of the second link 2302b. This pattern may be repeated along the length of the wrist 2300. In some embodiments, maintaining the wrist 2300 intact may require use of the sheath 1607 referred to in FIG. 16, which may help prevent the side plates 2314a,b of each link 2302a-c from moving outward radially.

Mechanically Decoupled Closure Subsystem

FIG. 24 is an enlarged isometric view of the distal end of the surgical tool 1600 of FIG. 16, according to one or more additional embodiments. In the illustrated embodiment, the surgical tool 1600 includes an end effector 2402 that includes opposing jaws 2404a and 2404b configured to move between open and closed positions. In at least one embodiment, the end effector 2402 may comprise a harmonic vessel sealer, but could alternatively comprise other types of instruments with opposing jaws such as, but not limited to, a surgical stapler, tissue graspers, surgical scissors, clip appliers, needle drivers, a babcock including a pair of opposed grasping jaws, bipolar jaws (e.g., bipolar Maryland grasper, forceps, a fenestrated grasper, etc.), etc.

One or both of the jaws 2404a, 2404b may be configured to pivot the end effector 2402 between open and closed positions. In the illustrated example, the upper jaw 2404a is designed to rotate (pivot) relative to the lower jaw 2402b to actuate the end effector 2402 between an open, unclamped position and a closed, clamped position. In other embodiments, however, both jaws 2404a, 2404b may be configured to simultaneously move to pivot the jaws 2404a, 2404b between the open and closed positions, and may thus be referred to as "bifurcating" jaws.

An articulable wrist 2406 interposes and couples the end effector 2402 to the distal end of the shaft 1602. The wrist 2406 may be similar in some respects to the wrist 1606 of FIG. 16, or any of the other articulable wrists described herein, and may thus be configured to articulate in a single plane. Moreover, rotating (rolling) the shaft 1602 about its longitudinal axis $A_1$ allows the wrist 2406 to articulate and position the end effector 2402 at various desired orientations and locations relative to a surgical site.

As illustrated, the wrist 2406 may include a distal connector 2408a, a proximal connector 2408b, and a plurality of articulation links extending between the connectors 2408a, b, labeled in FIG. 24 as at least a first articulation link 2410a, a second articulation link 2410b, and a third articulation link 2410c. The distal connector 2408a may be configured to couple the wrist 2406 to the end effector 2402, and the proximal connector 2408b may be configured to couple the wrist 2406 to the distal end of the shaft 1602. The distalmost articulation link may be pivotably coupled to a proximal end of the distal connector 2408a, and the proximalmost articulation link may be pivotably coupled to a distal end of the proximal connector 2408b.

The articulation links, including articulation links 2410a-c, are capable of being pivotably interconnected and arranged in series between the distal and proximal connectors 2408a,b and otherwise along at least a portion of a longitudinal length 2412 of the wrist 2406. FIG. 24 only references three articulation links 2410a-c for purposes of discussion, but the wrist 2406 can include more than three, as illustrated. In the illustrated embodiment, the first and third articulation links 2410a,c exhibit the same design and configuration, while the second articulation link 2410b is different and axially interposes the first and third articulation links 2410a,c. Accordingly, the first and second articulation links 2410a,b are repeated in an alternating pattern along the length 2412 of the wrist 2406.

The wrist 2406 also includes the drive members or "articulation bands" 1708a,b (only the first articulation band 1708a is visible in FIG. 24) extending from the drive housing 1608 (FIG. 16) and terminating at the distal connector 2408a. The articulation bands 1708a,b are arranged on angularly opposite sides (positions) of the articulation links 2410a-c, and selective actuation of the articulation bands 1708a,b causes articulation of the wrist 2406 in one plane of motion, as generally described above. As discussed below, the articulation bands 1708a,b extend through portions of some or all of the articulation links 2410a-c as they extend along the longitudinal length 2412 of the wrist 2406.

The first articulation link 2410a may be pivotably coupled to the second articulation link 2410b at a first coupling interface 2414a, the second articulation link 2410b may be pivotably coupled to the third articulation link 2410c at a second coupling interface 2414b, and the first and third articulation links 2410a,c may be pivotably coupled at a third coupling interface 2414c. As illustrated, the third coupling interface 2414c axially interposes the first and second coupling interfaces 2414a,b and is otherwise arranged at a position located between the first and second coupling interfaces 2414a,b along the longitudinal length 2412. The coupling interfaces 2414a-c can comprise any of the joint mechanism designs and configurations mentioned herein. In the illustrated embodiment, the first and third coupling interfaces 2414a,c comprise a pin and aperture joint mechanism, and the third coupling interface 2414c comprises a lobe and slot joint mechanism, as generally described above.

In the illustrated embodiment, the surgical tool 1600 further includes a closure redirect mechanism 2416, also referred to as a "jaw closure mechanism," operable (actuatable) to open and close the jaws 2404a,b. A distal portion of the closure redirect mechanism 2416 axially interposes the end effector 2402 and the wrist 2406, and may form part of or otherwise be operatively coupled to the end effector 2402. As illustrated, the proximal portion of the closure redirect mechanism 2416 includes a first or "upper" transfer link 2418a and a second or "lower" transfer link 2418b. The upper and lower transfer links 2418a,b are configured to antagonistically move (axially or linearly translate) along the longitudinal axis $A_1$ to open and close the jaws 2404a,b. More specifically, the upper transfer link 2418a is pivotably coupled to the upper jaw 2404a at a pivot arm 2420 such that moving (axially translating) the upper transfer link 2418a proximally relative to the lower transfer link 2418b causes the upper jaw 2404a to pivot to the open position. In contrast, the lower transfer link 2418b defines a jaw slot 2422 and is pivotably coupled to the upper jaw 2404a at a jaw pin 2424 extending laterally outward from the upper jaw 2404a and received within the jaw slot 2422. As the lower transfer link 2418b moves (axially translates) proximally relative to the upper transfer link 2418a, sliding interaction between the jaw pin 2424 and the jaw slot 2422 causes the upper jaw 2404a to pivot to the closed position.

In some embodiments, the closure redirect mechanism 2416 includes one or more upper tension members (not shown) operable to move the upper transfer link 2418a proximally, and one or more lower tension members (not shown) operable to move the lower transfer link 2418b proximally. The tension members extend from the shaft 1602, through the wrist 2406, and terminate at the corresponding transfer links 2418a,b. Example operation of the tension members to actuate the closure redirect mechanism 2416 will be described in more detail below.

FIGS. 25A and 25B are cross-sectional end views of the first and second articulation links 2410a and 2410b, respectively, according to one or more embodiments. As indicated above, the first articulation link 2410a may exhibit the same design and configuration as the third articulation link 2410c (FIG. 24). Consequently, discussion of the first articulation link 2410a is equally applicable to the third articulation link 2410c.

As illustrated, each articulation link 2410a,b may have a generally circular body 2502 and a central axis 2504 extends through the middle (center) of the body 2502. The body 2502 defines a central aperture 2506 aligned concentrically with the central axis 2504. The central aperture 2506 may be sized to receive a central member 2508 (shown in dashed lines) extending from the drive housing 1608 (FIG. 16), such as a transducer cable, a harmonic ribbon segment, a feedbar for a surgical stapler, or one or more drive members extending to the end effector 2402 (FIG. 24).

The body 2502 may further define opposing band lumens 2510 provided at angularly opposite positions (locations) of the body 2502. The articulation bands 1708a,b may be received within and otherwise extend through the band lumens 2510, respectively. When the wrist 2406 (FIG. 24) is assembled, the band lumens 2510 of each articulation link 2410a,b may axially align such that the articulation bands 1708a,b can pass therethrough in a relatively direct course along the entire length 2412 (FIG. 24) of the wrist 2406.

The body 2502 may further include joint mechanisms 2512 provided at angularly opposite positions of the body 2502, where each joint mechanism 2512 is 90° angularly offset from the band lumens 2510. Each joint mechanism 2512 forms part of a corresponding coupling interface, such as the coupling interfaces 2414a-c of FIG. 24. Accordingly, each joint mechanism 2512 may assume a variety of designs and configurations that facilitate a proper coupling interface that allows interconnected, serial articulation links 2410a-c (FIG. 24) to pivot (rotate) in a single plane.

The body 2502 may further define a pair of upper tensioning lumens 2514a and a pair of lower tensioning lumens 2514b. The upper tensioning lumens 2514a are sized to receive upper tension member(s) 2516a, and the lower tensioning lumens 2514b are sized to receive lower tension member(s) 2516b. The upper and lower tension members 2516a,b are operable to move the upper and lower transfer links 2418a,b (FIG. 24) proximally when actuated, and thereby actuate the end effector 2404 (FIG. 24). The tension members 2516a,b can include, for example, cables, lines, cords, wires, ropes, strings, twisted strings, or any elongate member capable of being placed in tension. When the articulation links 2410a,b are pivotably connected and arranged in series, the upper and lower tensioning lumens 2514a,b of each link 2410a,b will be aligned in series and thereby capable of receiving the upper and lower tension members 2516a,b along the entire length 2412 (FIG. 24) of the wrist 2406 (FIG. 24).

The upper tensioning lumens 2514a are defined on opposing sides of the body 2502 and are angularly located between the joint mechanism 2512 on the upper portion of the body 2502 and the opposing band lumens 2510. Similarly, the lower tensioning lumens 2514b are defined on opposing sides of the body 2502 and are angularly located between the joint mechanism 2512 on the lower portion of the body 2502 and the opposing band lumens 2510. Accordingly, the tension members 2516a,b extend axially through the body 2502 at locations angularly positioned between the band lumens 2510 and a neutral bending (rotation) axis 2518 for each articulation link 2410a,b, where the neutral bending axis 2518 is the axis about which the interconnected articulation links 2410a,b can pivot during operation.

The serially arranged articulation links 2410a-c (FIG. 24) of the wrist 2406 (FIG. 24) facilitates a kinematically deterministic articulation, which results in a consistent or known position of the end effector 2402 (FIG. 24) during operation. The joint mechanisms 2512 are located at corresponding areas 2520 aligned with the neutral bending axis 2518, and thus take up that space (e.g., area of the body 2502) for the kinematic coupling links. As a result, the area 2520 at the neutral bending axis 2518 is not available for the upper and lower tension members 2516a,b, which would otherwise be the most preferential routing configuration to minimize mechanical crosstalk between the articulation links 2402a-c and an adjacent function of the end effector 2402 (FIG. 24), such as closure. The embodiments described herein reduce or prevent mechanical crosstalk between the articulation links 2402a-c (FIG. 24) and the end effector 2402.

Figure 26:
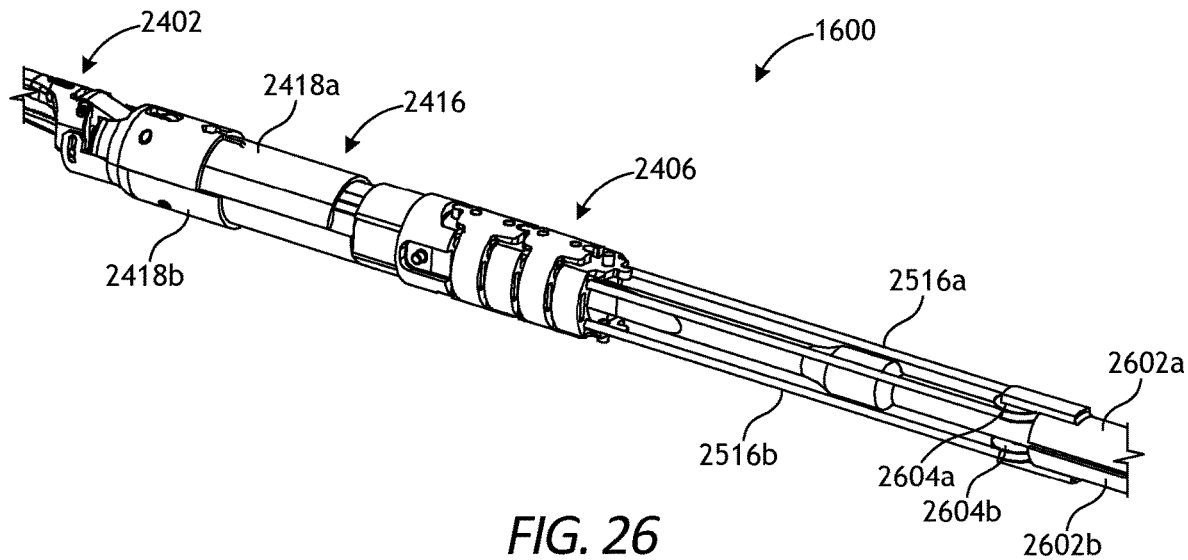
FIG. 26 is an enlarged isometric view of the distal end of the surgical tool of FIG. 16, according to one or more additional embodiments.

FIG. 26 is an enlarged isometric view of the distal end of the surgical tool 1600, according to one or more additional embodiments. The shaft 1602 (FIG. 24) and portions of the articulable wrist 2406 are omitted to enable viewing of various proximal parts of the closure redirect mechanism 2416. More specifically, proximal portions of the closure redirect mechanism 2416 may include an upper rigid link 2602a and a lower rigid link 2602b arranged proximally from the wrist 2406. In at least one embodiment, the upper and lower rigid links 2602a,b may each be housed within the shaft 1602 (not shown). An upper transfer mechanism 2604a is rotatably mounted to the upper rigid link 2602a and a lower transfer mechanism 2604b is rotatably mounted to the lower rigid link 2602b. In the illustrated embodiment, the upper and lower transfer mechanisms 2604a,b each comprise rotatable pulleys mounted to the corresponding rigid links 2602a,b. As described in more detail below, however, the transfer mechanisms 2604a,b can comprise other types of devices or systems, without departing from the scope of the disclosure.

The upper tension member 2516a extends to and is operatively coupled to the upper transfer mechanism 2604a such that axial movement of the upper rigid link 2602a correspondingly moves (translates) the upper tension member 2516a in the same axial direction. Similarly, the lower tension member 2516b extends to and is operatively coupled to the lower transfer mechanism 2604b such that axial movement of the lower rigid link 2602b correspondingly moves (translates) the lower tension member 2516b in the same axial direction. The transfer mechanisms 2604a,b are shown as pulleys in the illustrated embodiment, and the tension members 2516a,b in this embodiment are configured to wrap around the corresponding transfer mechanism 2604a,b. The distal ends of the upper tension member 2516a extend through the wrist 2406 and are fastened to the upper transfer link 2418a, and the distal ends of the lower tension member 2516b extend through the wrist 2406 and are fastened to the lower transfer link 2418b. Mechanical decoupling of the tension members 2516a,b relative the articulable wrist 2406 is accomplished by evenly distributing the loads and the displacement between the tension members 2516a,b on each side of the neutral axis of the wrist 2406 via the transfer mechanisms 2604a,b.

Figure 27A:
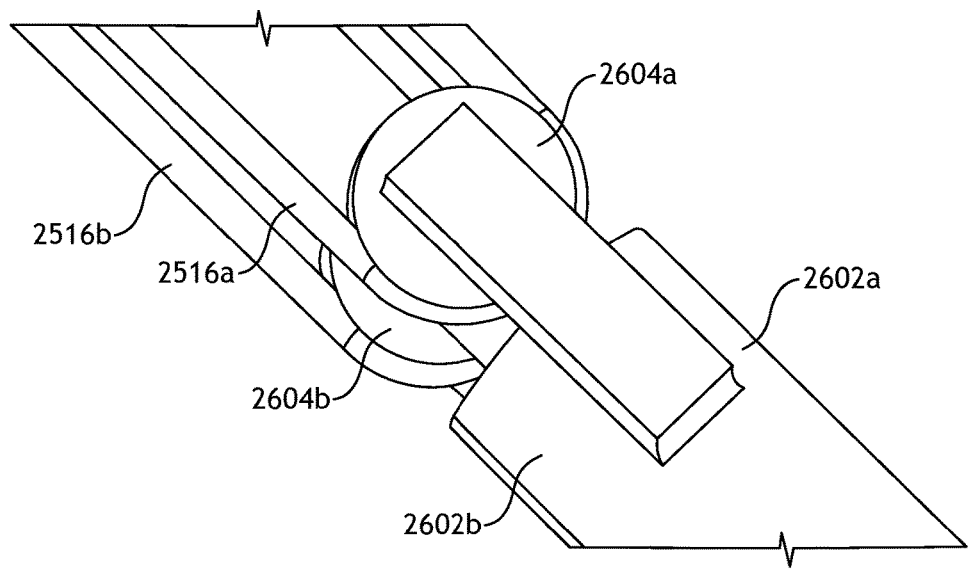
FIGS. 27A and 27B are enlarged views of the rigid links and the pulleys of FIG. 26, according to one or more embodiments.
Figure 27B:
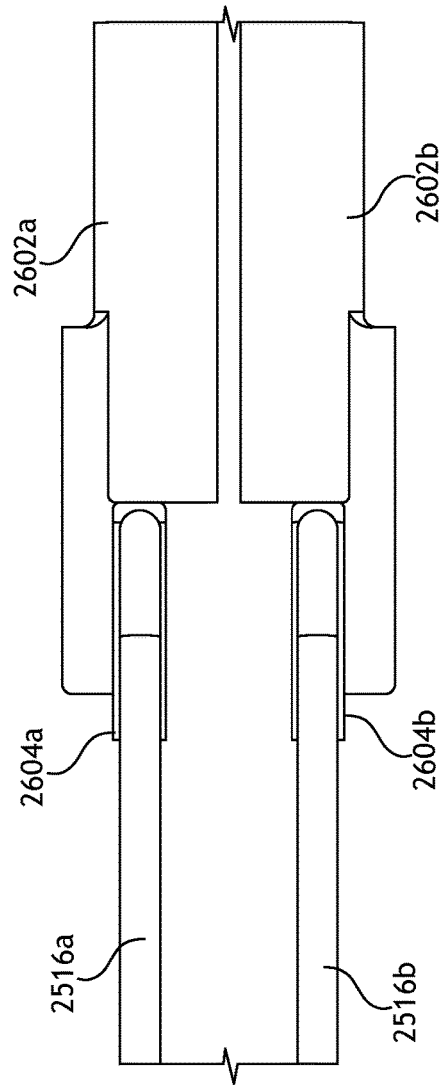

FIGS. 27A and 27B are enlarged views of the rigid links 2602a,b and the transfer mechanisms 2604a,b, according to one or more embodiments. Each transfer mechanism 2604a,b is rotatably coupled and grounded to a corresponding one of the rigid links 2602a,b. The rigid links 2602a,b, in cooperation with the transfer mechanisms 2604a,b, maintain the corresponding tension members 2516a,b in tension during operation. Moreover, the rigid links 2602a,b are capable of moving independent of the other (proximally and distally) as acted upon by the actuation system housed within the carriage 1616 (FIG. 16). Movement of a corresponding one of the rigid links 2602a,b translates actuation forces for clamping at the end effector 2402 from the proximal end of the surgical tool 1600 (e.g., the carriage 1616) to the tension members 2516a,b.

Figure 28:
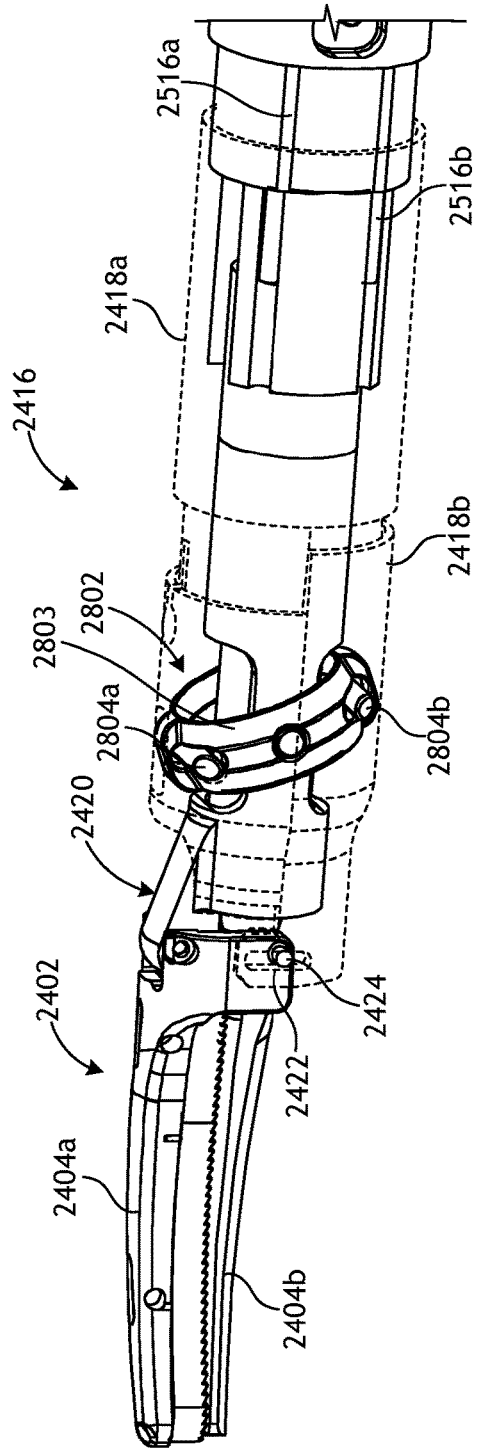
FIG. 28 is an enlarged view of the closure redirect mechanism of FIG. 24, according to one or more embodiments.

FIG. 28 is an enlarged view of the distal portions of the closure redirect mechanism 2416, according to one or more embodiments. As indicated above, the distal ends of the upper tension member 2516a are affixed to the upper transfer link 2418a (shown in dashed lines), and the distal ends of the lower tension member 2516b are affixed to the lower transfer link 2418b (shown in dashed lines). As also indicated above, the upper transfer link 2418a is pivotably coupled to the upper jaw 2404a at the pivot arm 2420 such that moving (axially translating) the upper transfer link 2418a proximally relative to the lower transfer link 2418b causes the upper jaw 2404a to pivot to the open position. Moreover, the lower transfer link 2418b is pivotably coupled to the upper jaw 2404a via interaction between the jaw pin 2424 extending from the upper jaw 2404a and received within the jaw slot 2422 defined in the lower transfer link 2418b. Consequently, proximal movement of the lower transfer link 2418b causes the upper jaw 2404a to pivot to the closed position. The lower transfer link 2404b accordingly differs from the upper transfer link 2404a in that it has two distal connection points.

As illustrated, the closure redirect mechanism 2416 further includes a circular rocker joint 2802 arranged within and pivotably mounted to both transfer links 2418a,b. The circular rocker joint 2802 provides a generally annular body 2803. A first or "upper" pivot axle 2804a pivotably couples an upper hemisphere of the circular rocker joint 2802 to the upper transfer link 2418a. Similarly, a second or "lower" pivot axle 2804b pivotably couples a lower hemisphere of the circular rocker joint 2802 to the lower transfer link 2418b. Consequently, as the upper transfer link 2418a is urged proximally via tensile loading of the upper tension member 2516a, the lower transfer link 2418b may be simultaneously urged distally via the circular rocker joint 2802, which pivotably couples the upper and lower transfer links 2418a,b. Similarly, as the lower transfer link 2418b is urged proximally via tensile loading of the lower tension member 2516b, the upper transfer link 2418a may be simultaneously urged distally via the pivotable coupling of the circular rocker joint 2802. Accordingly, the upper and lower transfer links 2418a,b may operate antagonistically to open or close the upper jaw 2404a. Moreover, the pivot arm 2420 and the circular rocker joint 2802 are both grounded to the distal end of the articulable wrist 2406, which transfers closure loads back down the shaft 1602 (FIG. 16) of the surgical tool 1600 (FIG. 16).

Referring again to FIG. 26, with continued reference to FIG. 28, example operation of the closure redirect mechanism 2416 is now provided. Differential loads and/or displacements are applied to the upper and lower rigid links 2602a via the proximal end of the tool 1600; e.g., from the drive housing 1608 (FIG. 16). The inter-linked transfer mechanisms 2604a,b, the tension members 2516a,b, and the transfer links 2418a,b are displaced accordingly as acted upon by the actuation systems included in the carriage 1616 (FIG. 16). The circular rocker joint 2802 differentiates and balances the loads on the upper and lower transfer links 2418a,b, with the net moment resulting in opening or closing of the upper jaw 2404a.

Moreover, as the articulable wrist 2406 articulates and otherwise moves through its range of motion, the length of the tension members 2516a,b will correspondingly change on the inside and outside of the articulation curve, but such length changes are differentiated by the transfer mechanisms 2604a,b with no net change on the lengths of the upper and lower transfer links 2418a,b, thereby decoupling closure control.

Alternative Embodiments

The proximal end of the closure redirect mechanism 2416 described with reference to FIGS. 26, 27A-27B, and 28 includes the upper and lower rigid links 2602a,b, each of which transfers loads and displacements from the proximal end of the surgical tool 1600 (FIG. 16) to the differentiating transfer mechanisms 2604a,b. It is contemplated herein that the rigid links 2602a,b could be replaced with cables sized appropriately and of adequate construction to minimize compliance.

Moreover, the proximal end of the closure redirect mechanism 2416 incorporates the differentiating transfer mechanisms 2604a,b to provide load and/or displacement sharing between the tension members 2516a,b running through the wrist 2406. It is contemplated herein to replace the transfer mechanisms 2604a,b shown in FIGS. 26 and 27A-27B with other devices or configurations.

FIG. 29A, for example, depicts another embodiment of the proximal end of the closure redirect mechanism 2416, which includes a rigid link 2902 and a transfer mechanism 2904 rotatably (pivotably) mounted to the rigid link 2902. The rigid link 2902 could replace either of the rigid links 2602a,b, and the transfer mechanism 2904 could replace either of the transfer mechanisms 2604a,b. In the illustrated embodiment, the transfer mechanism 2904 includes a pinion gear 2906 rotatably mounted to the rigid link 2902, and first and second racks 2908a and 2908b are matable with the pinion gear 2906. Lengths of a tension member, such as the upper tension member 2506a, extend distally from the first and second racks 2908a,b to be fixed to the distal portions of the closure redirect mechanism 2416. The racks 2908a,b are rigidly affixed to the corresponding lengths of the tension member 2516a, and the pinion gear 2906 is grounded, but rotatably mounted, to the rigid link 2902.

FIG. 29B depicts another embodiment of the proximal end of the closure redirect mechanism 2416, which includes the rigid link 2902 and a transfer mechanism 2910 rotatably (pivotably) mounted to the rigid link 2902. In the illustrated embodiment, the transfer mechanism 2910 comprises a rocker link 2912 pivotably mounted to the rigid link 2902. Lengths of a tension member, such as the upper tension member 2506a, extend distally from the rocker link 2912 to be fixed to the distal portions of the closure redirect mechanism 2416. The rocker link 2912 has a central pivot grounded to the rigid link 2902, and its ends are affixed to the opposing lengths of the tension member 2506a.

Articulation Band Length Conservation

The presently disclosed articulable wrists include band lumens provided at angularly opposite positions of each articulation link in the wrist. As described herein, upon pivotably coupling the articulation links in series, the band lumens of each articulation link align such that articulation members or "bands" can pass therethrough in a relatively direct course. The articulation bands are not bound within the band lumens, which allows the articulation bands to axially translate relative to the articulation links during operation, and thereby facilitates articulation of the wrist in at least one plane of motion.

During example operation, the articulable wrists described herein are actuated by pulling on one articulation band, while allowing slack in (i.e., releasing) the opposing articulation band. This creates an antagonistic give-and-take control of the wrist, but can also create problems in the control scheme related to length conservation of the articulation bands. Length conservation is essentially the difference in length between the opposing articulation bands to make sure the wrist stays antagonistic. Length conservation between the articulation bands as the wrist articulates one way or the other is critical to be as close to zero as possible (if not zero).

As described herein, the articulable wrists can be designed such that the articulation bands maintain tension through the entire articulation of the wrist, which gives true antagonistic motion without lagging when changing direction. One way to accomplish this is by maintaining the same spacing from the centerline of the linkages, which may be important for starting off with a good baseline. The linkage kinematic diagram may then be mimicked with straight lumens (i.e., band lumens) in the linkage. Moreover, forcing length changes outside of the lumen can maintain length conservation in a perfect straight line theoretical sense.

Figure 30:
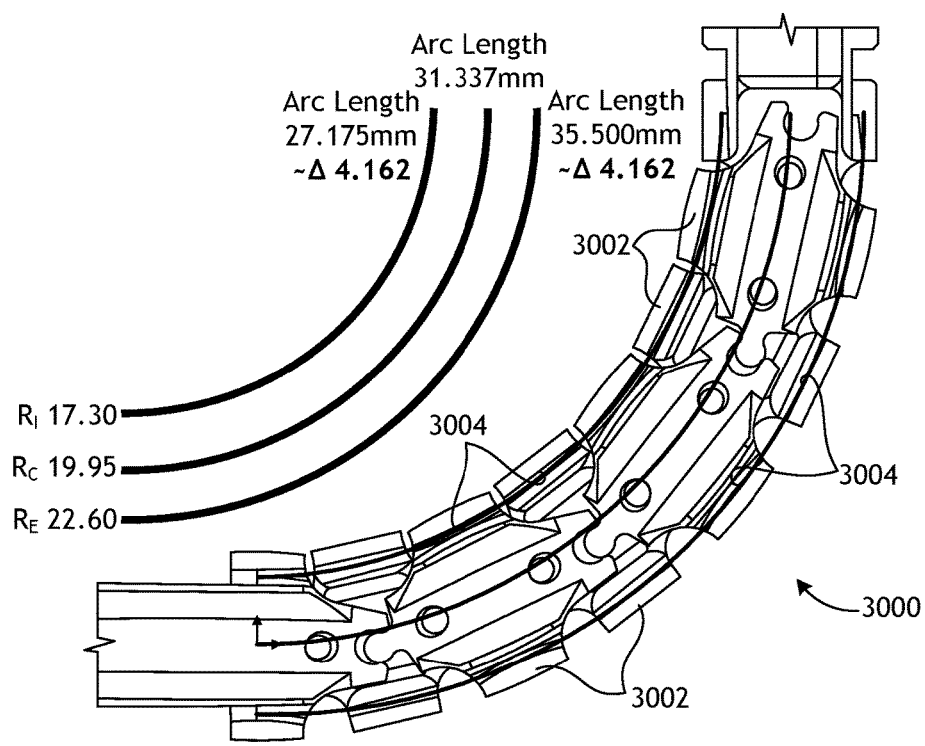
FIG. 30 is a cross-sectional side view of an example articulable wrist, and showing illustrative arc length parameters, according to one or more embodiments.

FIG. 30 is a cross-sectional side view of an example articulable wrist 3000, and showing illustrative arc length parameters, according to one or more embodiments. As illustrated, the wrist 3000 includes a plurality of articulation linkages 3002, and each articulation linkage 3002 defines or otherwise provides opposing band lumens 3004 defined on opposite angular locations of each articulation linkage 3002. The design and configuration of the band lumens 3004 may be intended to eliminate stress concentrations on the articulation bands (not shown) extending therethrough. In the illustrated embodiment, the band lumens are defined and otherwise contoured to the natural arc that the articulation bands might take in a fully articulated (90°) state. This results in creating more contact area between the articulation band and the corresponding articulation linkages 3002.

Articulation band length conservation can be determined based on the following mathematical equations:

$$\text{Offset}_{Band} = R_C - R_I = R_E - R_C$$

where $R_C$ is the radius at the center of the wrist 3000, $R_I$ is the radius "intrados" or the radius at the inner curve of the wrist 3000, and $R_E$ is the radius "extrados" or the radius at the outer curve of the wrist 3000.

$$2\pi R_C \frac{90}{360} - 2\pi R_I \frac{90}{360} = \text{Pull}$$

$$2\pi R_E \frac{1}{4} - 2\pi R_C \frac{1}{4} = \text{Release}$$

$$\frac{\pi}{2}(R_C - R_I) = \text{Pull}$$

$$\frac{\pi}{2}(R_E - R_C) = \text{Release}$$

$$\frac{\pi}{2}(O_{Band}) = \text{Pull}$$

$$\frac{\pi}{2}(O_{Band}) = \text{Release}$$

Figure 31:
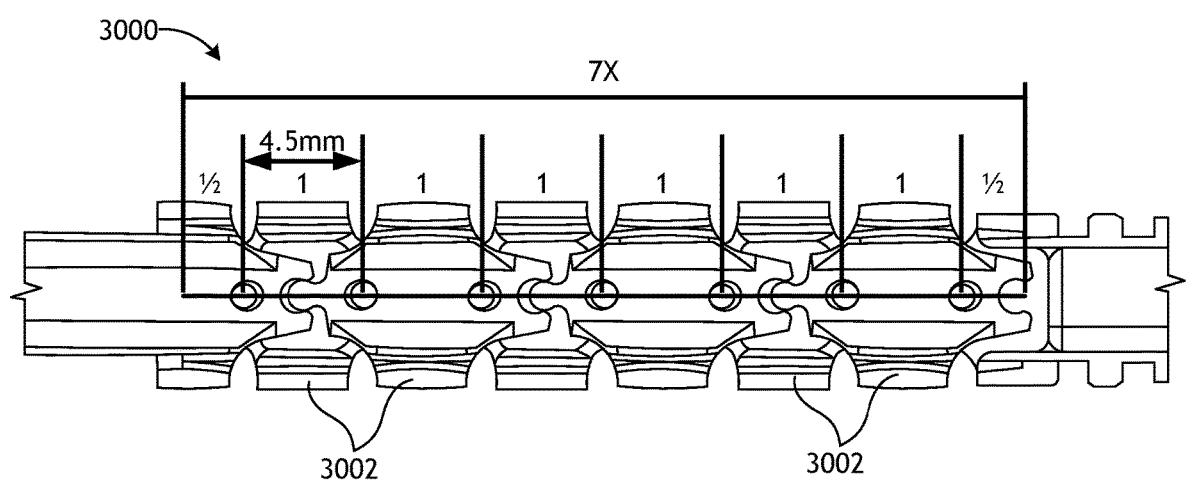
FIG. 31 is a side view of the articulable wrist of FIG. 30 showing example measurements of the lengths of the articulation linkages.

The foregoing equations demonstrate that if the articulation band location relative to the centerline of the wrist 3000 is not the same, then there will be a deviation from length conservation. Both articulation bands being under tension will pull them to the intrados (inner) side of the band lumen 3004, which will increase the pull amount and decrease the release amount. The discrepancy stems from where the neutral length of the articulation bands is derived. The arc length assumption assumes that length conservation is based on a deviation from the instrument perfect arc centerline when articulated. In reality, however, and as graphically depicted in FIG. 31, the neutral length of the articulation bands is defined in the straight configuration in which the length is defined by the lengths of the articulation linkages 3002 rather than a curve at the centerline. In other words, the centerline arc is an under-approximation of the neutral length.

$$4.5 \text{ mm} \times 7 \text{ linkages} = 31.5 \text{ mm}$$

$$31.5 - 31.337 = 0.163$$

$$\frac{\pi}{2}(R_C - R_I) = \text{Pull}$$

$$\frac{\pi}{2}(R_E - R_C) = \text{Release}$$

Since the difference between the linkage lengths and the centerline arc (31.337) is a difference of 0.163 mm, this increases how much of the articulation band needs to be pulled and decreases how much the opposing articulation band needs to be let out (released), thus doubling the 0.163 mm difference and resulting in a total discrepancy from length conservation of 0.326 mm.

The approach to achieve more length conservation centers around the direction of the articulation bands mimicking the kinematics of the articulation linkages 3002 rather than following arcs. More contact points along with the already increased number of articulation linkages may alleviate kinking of the articulation bands. This approximation relies on the articulation bands being straight inside of the articulation linkages 3002. This drives the change in length only to the gaps between the articulation linkages 3002, where similar triangles prove that the amount pulled is equal to the amount let out (slackened). This assumption may be valid in embodiments where the band lumens 3004 are the same distance from the centerline, and the exit/entry to the band lumens 3004 defined by each articulation linkage 3002 is the same axial distance from the pivot.

Figure 32:
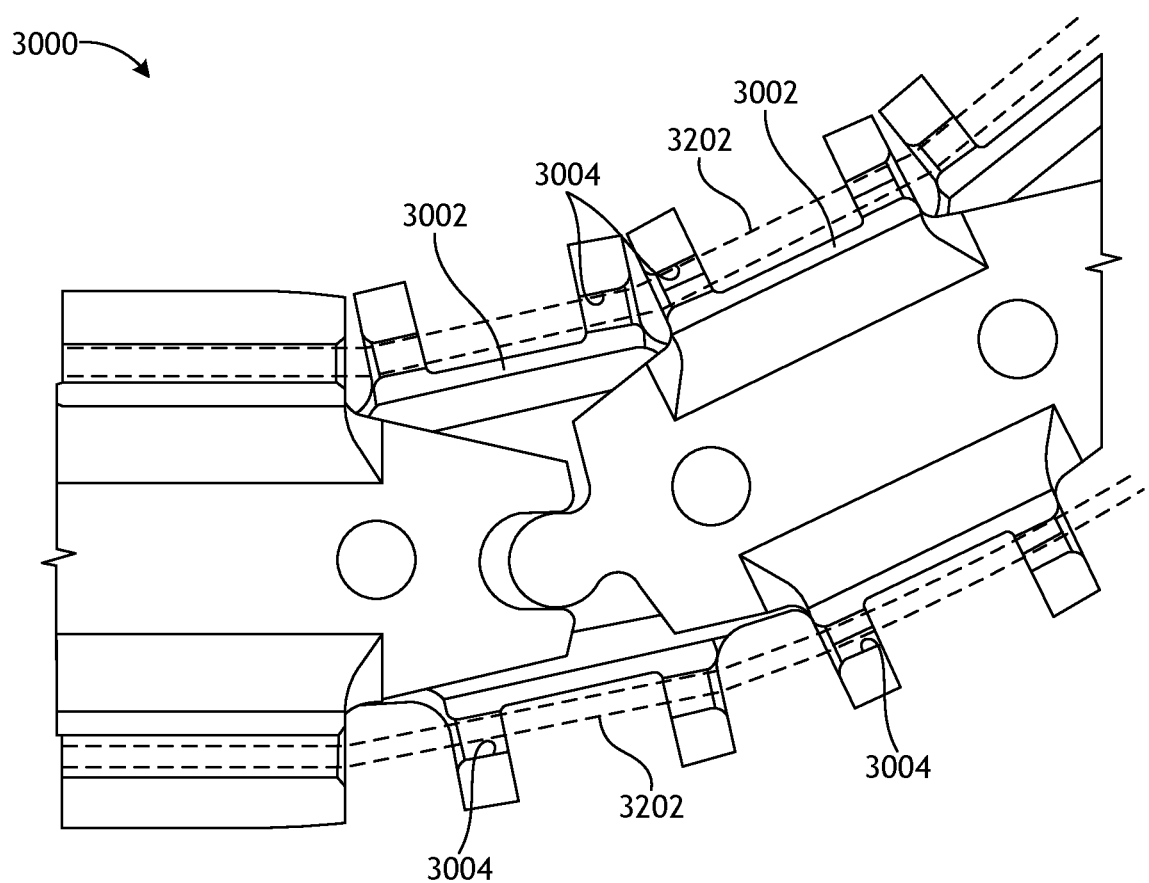
FIG. 32 is an enlarged cross-sectional side view of a portion of the articulable wrist of FIG. 30.

FIG. 32 is an enlarged cross-sectional side view of a portion of the articulable wrist 3000 of FIG. 30. FIG. 32 also shows in dashed lines example articulation bands 3202 extended through the corresponding band lumens 3004 on opposite angular locations of the articulation linkages 3002. Applying this concept to the articulation bands 3202 may require more of a spline approximation with contact points at the entry/exit of each band lumen 3004. With these contact points, the spline approximation significantly decreases the length conservation deviation.

In at least one embodiment, to accomplish this type of contact at the entry/exit of the band lumens 3004, while simultaneously allowing for some spline arc through the entire wrist 3000, may require band lumens 3004 that exhibit a generally oval or "football-shaped" cross section. A cut from the external surface of the articulation linkages 3002 breaking through an otherwise straight band lumen 3004 may give enough relief for the spline arc, while maintaining the contact points at the entry/exit of the band lumens 3004.

Embodiments disclosed herein include:

A. A surgical tool that includes an elongate shaft, an end effector arranged at a distal end of the elongate shaft and including opposing first and second jaws, and an articulable wrist interposing the end effector and the elongate shaft and comprising a plurality of articulation links arranged in series along a longitudinal length of the articulable wrist. The surgical tool further including a closure redirect mechanism including first and second rigid links arranged proximal to the articulable wrist, first and second transfer mechanisms pivotably mounted to the first and second rigid links, respectively, first and second transfer links interposing the end effector and the articulable wrist, and first and second tension members extending distally from the first and second transfer mechanisms, respectively, and being secured to the first and second transfer links, respectively, wherein moving the first rigid link relative to the second rigid link, and vice versa, causes the first and second transfer links to correspondingly move and thereby open or close the opposing first and second jaws.

B. A closure redirect mechanism for a surgical tool includes first and second rigid links arranged proximal to an articulable wrist of the surgical tool, first and second transfer mechanisms pivotably mounted to the first and second rigid links, respectively, first and second transfer links interposing the articulable wrist and an end effector of the surgical tool, the end effector including opposing first and second jaws, and first and second tension members extending distally from the first and second transfer mechanisms, respectively, and being secured to the first and second transfer links, respectively, wherein moving the first rigid link relative to the second rigid link, and vice versa, causes the first and second transfer links to correspondingly move and thereby open or close the opposing first and second jaws.

Each of embodiments A and B may have one or more of the following additional elements in any combination: Element 1: wherein the end effector is selected from the group consisting of a harmonic vessel sealer, a surgical stapler, a tissue grasper, surgical scissors, a clip applier, a needle driver, a babcock, bipolar jaws, and any combination thereof. Element 2: wherein the first transfer link is pivotably coupled to the first jaw at a pivot arm such that moving the first transfer link proximally relative to the second transfer link causes the first jaw to pivot to an open position, and wherein the second transfer link is pivotably coupled to the first jaw such that moving the second transfer link proximally relative to the first transfer link causes the first jaw to pivot to a closed position. Element 3: wherein the first and second rigid links are arranged within the elongate shaft. Element 4: wherein the plurality of articulation links includes a first articulation link, a second articulation link, and a third articulation link, the first articulation link being pivotably coupled to the second articulation link at a first coupling interface, the second articulation link being pivotably coupled to the third articulation link at a second coupling interface, and the first and third articulation links being pivotably coupled at a third coupling interface, and wherein the third coupling interface axially interposes the first and second coupling interfaces along the longitudinal length of the articulable wrist. Element 5: wherein each articulation link comprises a circular body that defines a central aperture, joint mechanisms provided at opposite angular locations of the circular body, each joint mechanism forming part of a corresponding coupling interface, band lumens defined in the circular body at angularly opposite positions and 90° offset from the joint mechanisms, the band lumens being sized to receive corresponding articulation bands that extend along the longitudinal length of the articulable wrist, a pair of upper tensioning lumens defined in the circular body and sized to receive distally extending portions of the first tension member, and a pair of lower tensioning lumens defined in the circular body and sized to receive distally extending portions of the second tension member. Element 6: wherein the upper tensioning lumens are angularly located between the band lumens and a joint mechanism on an upper portion of the circular body, and the lower tensioning lumens are angularly located between the band lumens and a joint mechanism on a lower portion of the circular body. Element 7: wherein a neutral bending axis extends through each coupling interface when the plurality of articulation links are pivotably coupled and arranged in series, and wherein the upper tensioning lumens are located on an upper portion of the circular body between the band lumens and the neutral bending axis, and the lower tensioning lumens are located on a lower portion of the circular body between the band lumens and the neutral bending axis. Element 8: wherein the central aperture is sized to receive a central member extending from a drive housing of the surgical tool. Element 9: wherein the closure redirect mechanism further includes a circular rocker joint providing upper and lower hemispheres, the first transfer link being pivotably coupled to the upper hemisphere, and the second transfer link being pivotably coupled to the lower hemisphere.

Element 10: wherein moving the first transfer link proximally simultaneously moves the second transfer link distally via the circular rocker joint, and wherein moving the second transfer link proximally simultaneously moves the first transfer link distally via the circular rocker joint. Element 11: wherein each transfer mechanism comprises a rotatable pulley mounted to the first and second rigid links, respectively, and wherein the first and second tension members wrap around the rotatable pulley and distal ends of the first and second tension members extend distally from the rotatable pulley to be secured to the first and second transfer links, respectively.

Element 12: wherein the first transfer link is pivotably coupled to the first jaw at a pivot arm such that moving the first transfer link proximally relative to the second transfer link causes the first jaw to pivot to an open position, and wherein the second transfer link is pivotably coupled to the first jaw such that moving the second transfer link proximally relative to the first transfer link causes the first jaw to pivot to a closed position. Element 13: wherein a jaw pin extends from the first jaw and the second transfer link defines a jaw slot that receives the jaw pin to pivotably couple the second transfer link to the first jaw. Element 14: wherein the closure redirect mechanism further includes a circular rocker joint providing upper and lower hemispheres, the first transfer link being pivotably coupled to the upper hemisphere, and the second transfer link being pivotably coupled to the lower hemisphere. Element 15: wherein moving the first transfer link proximally simultaneously moves the second transfer link distally via the circular rocker joint, and wherein moving the second transfer link proximally simultaneously moves the first transfer link distally via the circular rocker joint. Element 16: wherein each transfer mechanism comprises a rotatable pulley mounted to the first and second rigid links, respectively, and wherein the first and second tension members wrap around the rotatable pulley and distal ends of the first and second tension members extend distally from the rotatable pulley to be secured to the first and second transfer links, respectively. Element 17: wherein each transfer mechanism comprises a pinion gear rotatably mounted to a corresponding one of the first and second rigid links, first and second racks matable with the pinion gear, first and second lengths of the first tension member extending from the first and second racks matable with the pinion gear mounted to the first rigid link, and first and second lengths of the second tension member extending from the first and second racks matable with the pinion gear mounted to the second rigid link. Element 18: wherein each transfer mechanism comprises a rocker link pivotably mounted to a corresponding one of the first and second rigid links, first and second lengths of the first tension member extending from the rocker link pivotably mounted to the first rigid link, and first and second lengths of the second tension member extending from the rocker link pivotably mounted to the second rigid link.

By way of non-limiting example, exemplary combinations applicable to A and B include: Element 4 with Element 5; Element 4 with Element 6; Element 6 with Element 7; Element 6 with Element 8; Element 6 with Element 9; Element 9 with Element 10; Element 12 with Element 13; and Element 14 with Element 15.

3. Implementing Systems and Terminology.

Implementations disclosed herein provide systems, methods and apparatus for instruments for use with robotic systems. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification, which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A surgical tool, comprising:
an elongate shaft;
an end effector arranged at a distal end of the elongate shaft and including opposing first and second jaws;
an articulable wrist interposing the end effector and the elongate shaft and comprising a plurality of articulation links arranged in series along a longitudinal length of the articulable wrist; and a closure redirect mechanism including:
- first and second rigid links arranged proximal to the articulable wrist;
- first and second transfer mechanisms pivotably mounted to the first and second rigid links, respectively;
- first and second transfer links interposing the end effector and the articulable wrist; and
- first and second tension members extending distally from the first and second transfer mechanisms, respectively, and being secured to the first and second transfer links, respectively,
- wherein moving the first rigid link relative to the second rigid link, and vice versa, causes the first and second transfer links to correspondingly move and thereby open or close the opposing first and second jaws.

2. The surgical tool of claim 1, wherein the end effector is selected from the group consisting of a harmonic vessel sealer, a surgical stapler, a tissue grasper, surgical scissors, a clip applier, a needle driver, a babcock, bipolar jaws, and any combination thereof.

3. The surgical tool of claim 1, wherein the first transfer link is pivotably coupled to the first jaw at a pivot arm such that moving the first transfer link proximally relative to the second transfer link causes the first jaw to pivot to an open position, and
wherein the second transfer link is pivotably coupled to the first jaw such that moving the second transfer link proximally relative to the first transfer link causes the first jaw to pivot to a closed position.

4. The surgical tool of claim 1, wherein the first and second rigid links are arranged within the elongate shaft.

5. The surgical tool of claim 1, wherein the plurality of articulation links includes a first articulation link, a second articulation link, and a third articulation link, the first articulation link being pivotably coupled to the second articulation link at a first coupling interface, the second articulation link being pivotably coupled to the third articulation link at a second coupling interface, and the first and third articulation links being pivotably coupled at a third coupling interface, and
wherein the third coupling interface axially interposes the first and second coupling interfaces along the longitudinal length of the articulable wrist.

6. The surgical tool of claim 5, wherein each articulation link comprises:
- a circular body that defines a central aperture;
- a first and a second joint mechanism provided at opposite angular locations of the circular body, each joint mechanism forming part of a corresponding coupling interface;
- band lumens defined in the circular body at angularly opposite positions and 90° offset from the joint mechanisms, the band lumens being sized to receive corresponding articulation bands that extend along the longitudinal length of the articulable wrist;
- a pair of upper tensioning lumens defined in the circular body and sized to receive distally extending portions of the first tension member; and
- a pair of lower tensioning lumens defined in the circular body and sized to receive distally extending portions of the second tension member.

7. The surgical tool of claim 6, wherein the upper tensioning lumens are angularly located between the band lumens and the first joint mechanism on an upper portion of the circular body, and the lower tensioning lumens are angularly located between the band lumens and the second joint mechanism on a lower portion of the circular body.

8. The surgical tool of claim 6, wherein a neutral bending axis extends through each coupling interface when the plurality of articulation links are pivotably coupled and arranged in series, and wherein the upper tensioning lumens are located on an upper portion of the circular body between the band lumens and the neutral bending axis, and the lower tensioning lumens are located on a lower portion of the circular body between the band lumens and the neutral bending axis.

9. The surgical tool of claim 6, wherein the central aperture is sized to receive a central member extending from a drive housing of the surgical tool.

10. The surgical tool of claim 1, wherein the closure redirect mechanism further includes a circular rocker joint providing upper and lower hemispheres, the first transfer link being pivotably coupled to the upper hemisphere, and the second transfer link being pivotably coupled to the lower hemisphere.

11. The surgical tool of claim 10, wherein moving the first transfer link proximally simultaneously moves the second transfer link distally via the circular rocker joint, and wherein moving the second transfer link proximally simultaneously moves the first transfer link distally via the circular rocker joint.

12. The surgical tool of claim 1, wherein each transfer mechanism comprises a rotatable pulley mounted to the first and second rigid links, respectively, and
wherein the first and second tension members wrap around the rotatable pulley and distal ends of the first and second tension members extend distally from the rotatable pulley to be secured to the first and second transfer links, respectively.

13. A closure redirect mechanism for a surgical tool, comprising:
- first and second rigid links arranged proximal to an articulable wrist of the surgical tool;
- first and second transfer mechanisms pivotably mounted to the first and second rigid links, respectively;
- first and second transfer links interposing the articulable wrist and an end effector of the surgical tool, the end effector including opposing first and second jaws; and
- first and second tension members extending distally from the first and second transfer mechanisms, respectively, and being secured to the first and second transfer links, respectively,
- wherein moving the first rigid link relative to the second rigid link, and vice versa, causes the first and second transfer links to correspondingly move and thereby open or close the opposing first and second jaws.

14. The closure redirect mechanism of claim 13, wherein the first transfer link is pivotably coupled to the first jaw at a pivot arm such that moving the first transfer link proximally relative to the second transfer link causes the first jaw to pivot to an open position, and
wherein the second transfer link is pivotably coupled to the first jaw such that moving the second transfer link proximally relative to the first transfer link causes the first jaw to pivot to a closed position.

15. The closure redirect mechanism of claim 14, wherein a jaw pin extends from the first jaw and the second transfer link defines a jaw slot that receives the jaw pin to pivotably couple the second transfer link to the first jaw.

16. The closure redirect mechanism of claim 13, wherein the closure redirect mechanism further includes a circular rocker joint providing upper and lower hemispheres, the first transfer link being pivotably coupled to the upper hemisphere, and the second transfer link being pivotably coupled to the lower hemisphere.

17. The closure redirect mechanism of claim 16, wherein moving the first transfer link proximally simultaneously moves the second transfer link distally via the circular rocker joint, and wherein moving the second transfer link proximally simultaneously moves the first transfer link distally via the circular rocker joint.

18. The closure redirect mechanism of claim 13, wherein each transfer mechanism comprises a rotatable pulley mounted to the first and second rigid links, respectively, and
wherein the first and second tension members wrap around the rotatable pulley and distal ends of the first and second tension members extend distally from the rotatable pulley to be secured to the first and second transfer links, respectively.

19. The closure redirect mechanism of claim 13, wherein each transfer mechanism comprises:
a pinion gear rotatably mounted to a corresponding one of the first and second rigid links;
first and second racks matable with the pinion gear;
first and second lengths of the first tension member extending from the first and second racks matable with the pinion gear mounted to the first rigid link; and
first and second lengths of the second tension member extending from the first and second racks matable with the pinion gear mounted to the second rigid link.

20. The closure redirect mechanism of claim 13, wherein each transfer mechanism comprises:
a rocker link pivotably mounted to a corresponding one of the first and second rigid links;
first and second lengths of the first tension member extending from the rocker link pivotably mounted to the first rigid link; and
first and second lengths of the second tension member extending from the rocker link pivotably mounted to the second rigid link.

21. A surgical tool, comprising:
an elongate shaft;
an end effector arranged at a distal end of the elongate shaft and configurable between an open configuration and a closed configuration;
an articulable wrist interposing the end effector and the elongate shaft;
first and second pulleys rotatably mounted within the elongate shaft;
first and second transfer links coupled to the end effector; and
first and second cables extending distally from the first and second pulleys, respectively, and being secured to the first and second transfer links, respectively,
wherein the end effector is transitionable:
toward the open configuration based on movement of the first transfer link relative to the second transfer link; and
toward the closed configuration based on movement of the second transfer link relative to the first transfer link.

* * * * *